(12) United States Patent
Raillard et al.

(10) Patent No.: US 9,290,445 B2
(45) Date of Patent: Mar. 22, 2016

(54) METHODS OF SYNTHESIZING A LEVODOPA ESTER PRODRUG

(75) Inventors: Stephen P. Raillard, Mountain View, CA (US); Adam Mann, Sunnyvale, CA (US); Suresh K. Manthati, Sunnyvale, CA (US); Randall A. Scheuerman, Santa Clara, CA (US); Tono Estrada, Santa Clara, CA (US); Mark Q. Nguyen, San Jose, CA (US); Cindy X Zhou, Palo Alto, CA (US)

(73) Assignee: XenoPort, Inc., Santa Clara, CA (US)

( * ) Notice: Subject to any disclaimer, the term of this patent is extended or adjusted under 35 U.S.C. 154(b) by 915 days.

(21) Appl. No.: 12/581,808

(22) Filed: Oct. 19, 2009

(65) Prior Publication Data

US 2010/0099907 A1  Apr. 22, 2010

Related U.S. Application Data

(60) Provisional application No. 61/106,930, filed on Oct. 20, 2008.

(51) Int. Cl.
| | |
|---|---|
| C07C 269/06 | (2006.01) |
| C07C 67/20 | (2006.01) |
| C07C 227/20 | (2006.01) |
| C07C 269/04 | (2006.01) |

(52) U.S. Cl.
CPC ........... *C07C 269/06* (2013.01); *C07C 67/20* (2013.01); *C07C 227/20* (2013.01); *C07C 269/04* (2013.01)

(58) Field of Classification Search
None
See application file for complete search history.

(56) References Cited

U.S. PATENT DOCUMENTS

| | | | |
|---|---|---|---|
| 3,811,444 A | 5/1974 | Heller et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien et al. |
| 4,038,411 A | 7/1977 | Saari |
| 4,066,747 A | 1/1978 | Capozza |
| 4,070,347 A | 1/1978 | Schmitt |
| 4,079,038 A | 3/1978 | Choi et al. |
| 4,083,949 A | 4/1978 | Benedikt |
| 4,093,709 A | 6/1978 | Choi et al. |
| 4,134,991 A | 1/1979 | Wermuth |
| 4,180,509 A | 12/1979 | Metcalf et al. |
| 4,311,706 A | 1/1982 | Bodor et al. |
| 4,663,349 A | 5/1987 | Repta |
| 4,771,073 A | 9/1988 | Repta |
| 4,826,875 A | 5/1989 | Chiesi |
| 4,873,263 A | 10/1989 | Repta |
| 4,879,303 A | 11/1989 | Davison et al. |
| 4,914,222 A | 4/1990 | Budavari et al. |

(Continued)

FOREIGN PATENT DOCUMENTS

| | | |
|---|---|---|
| CA | 2607198 | 11/2006 |
| DE | 10 2005 022 276 A1 | 11/2006 |

(Continued)

OTHER PUBLICATIONS http://en.wikipedia.org/wiki/Methylpyrrolidone.*

(Continued)

*Primary Examiner* — Sudhakar Katakam
*Assistant Examiner* — Jennifer C Sawyer

(57) ABSTRACT

Methods of synthesizing a levodopa ester prodrug, salts thereof, and synthetic intermediates thereof are disclosed.

24 Claims, 1 Drawing Sheet

(56) References Cited

U.S. PATENT DOCUMENTS

| | | | |
|---|---|---|---|
| 4,966,915 | A | 10/1990 | Tsuchiya et al. |
| 4,983,400 | A | 1/1991 | Dempski et al. |
| 5,017,607 | A | 5/1991 | Chiesi |
| 5,057,321 | A | 10/1991 | Edgren et al. |
| 5,073,641 | A | 12/1991 | Bundgaard et al. |
| 5,128,145 | A | 7/1992 | Edgren et al. |
| 5,133,974 | A | 7/1992 | Paradissis et al. |
| 5,190,763 | A | 3/1993 | Edgren et al. |
| 5,283,352 | A | 2/1994 | Backstrom et al. |
| 5,332,576 | A | 7/1994 | Mantelle |
| 5,462,933 | A | 10/1995 | Kramer et al. |
| 5,580,904 | A | 12/1996 | Ishikura et al. |
| 5,607,969 | A | 3/1997 | Milman et al. |
| 5,637,780 | A | 6/1997 | Jadhav et al. |
| 5,698,155 | A | 12/1997 | Grosswald et al. |
| 5,725,883 | A | 3/1998 | Staniforth et al. |
| 5,827,819 | A | 10/1998 | Yatvin et al. |
| 5,840,756 | A | 11/1998 | Cohen et al. |
| 6,696,600 | B2 | 2/2004 | Frenkel et al. |
| 7,008,950 | B1 | 3/2006 | Ohkawa et al. |
| 7,101,912 | B2 | 9/2006 | Xiang et al. |
| 7,144,877 | B2 | 12/2006 | Gallop et al. |
| 7,323,585 | B2 | 1/2008 | Xiang et al. |
| 7,342,131 | B2 | 3/2008 | Xiang et al. |
| 7,534,813 | B2 | 5/2009 | Xiang et al. |
| 7,563,821 | B2 | 7/2009 | Xiang et al. |
| 7,671,089 | B2 | 3/2010 | Xiang et al. |
| 7,709,527 | B2 | 5/2010 | Xiang et al. |
| 7,829,592 | B2 | 11/2010 | Xiang et al. |
| 7,893,105 | B2 | 2/2011 | Xiang et al. |
| 7,956,212 | B2 | 6/2011 | Xiang et al. |
| 7,968,597 | B2 | 6/2011 | Xiang et al. |
| 8,163,958 | B2 | 4/2012 | Xiang et al. |
| 2002/0099041 | A1 | 7/2002 | Gallop et al. |
| 2003/0152628 | A1 | 8/2003 | Licht et al. |
| 2003/0158254 | A1 | 8/2003 | Zerangue et al. |
| 2005/0209181 | A1 | 9/2005 | Akil et al. |
| 2005/0209246 | A1 | 9/2005 | Ueda et al. |
| 2005/0282891 | A1* | 12/2005 | Xiang et al. .......... 514/521 |
| 2006/0020028 | A1 | 1/2006 | Xiang et al. |
| 2007/0225366 | A1 | 9/2007 | Xiang et al. |
| 2008/0070984 | A1 | 3/2008 | Tran et al. |
| 2008/0103200 | A1 | 5/2008 | Xiang et al. |
| 2008/0132570 | A1 | 6/2008 | Xiang et al. |
| 2008/0171789 | A1 | 7/2008 | Xiang et al. |
| 2008/0214663 | A1 | 9/2008 | Xiang et al. |
| 2009/0137834 | A1 | 5/2009 | Xiang et al. |
| 2009/0156679 | A1 | 6/2009 | Xiang et al. |
| 2009/0326067 | A1 | 12/2009 | Xiang et al. |
| 2010/0099761 | A1 | 4/2010 | Karaborni et al. |
| 2010/0173992 | A1 | 7/2010 | Xiang et al. |
| 2010/0226855 | A1 | 9/2010 | Nangia et al. |
| 2011/0028544 | A1 | 2/2011 | Xiang et al. |
| 2011/0111024 | A1 | 5/2011 | Mao et al. |
| 2011/0111062 | A1 | 5/2011 | Xiang et al. |
| 2011/0201817 | A1 | 8/2011 | Xiang et al. |
| 2012/0190861 | A1 | 7/2012 | Xiang et al. |

FOREIGN PATENT DOCUMENTS

| | | |
|---|---|---|
| EP | 0309827 B1 | 4/1989 |
| GB | 1447599 | 8/1976 |
| GB | 1537951 | 1/1979 |
| JP | 58-024547 | 2/1983 |
| WO | 86/04579 | 8/1986 |
| WO | 98/01615 | 3/1988 |
| WO | 01/68065 A2 | 9/2001 |
| WO | 02/28882 A1 | 4/2002 |
| WO | 2005/121069 A1 | 12/2005 |
| WO | 2005/121070 A1 | 12/2005 |
| WO | 2007/067495 | 6/2007 |
| WO | 2007/087256 A2 | 8/2007 |
| WO | WO 2008/079387 A1 | 7/2008 |

OTHER PUBLICATIONS http://en.wikipedia.org/wiki/Methylpyrrolidone, 2012.*

International Search Report and Written Opinion of the International Searching Authority mailed Aug. 2, 2010, for PCT/US2009/005698.

Sasahara et al., Dosage form design for improvement of bioavailability of levodopa II: bioavailability of marketed levodopa preparations in dogs and Parkinsonian patients. *J Pharm. Sci* 1990, 69(3), 261-265.

Office Action mailed Nov. 24, 2006, for U.S. Appl. No. 11/145,159, filed Jun. 3, 2005.

Final Office Action mailed Jun. 15, 2007 for U.S. Appl. No. 11/145,159, filed Jun. 3, 2005.

Notice of Allowance mailed Oct. 10, 2007 for U.S. Appl. No. 11/145,159, filed Jun. 3, 2005.

Office Action mailed Jan. 19, 2007, for U.S. Appl. No. 11/145,280, filed Jun. 3, 2005.

Office Action mailed Apr. 17, 2007, for U.S. Appl. No. 11/145,280, filed Jun. 3, 2005.

Notice of Allowance, Notice of Allowability, and Examiner's Amendment mailed Sep. 11, 2007, for U.S. Appl. No. 11/145,280, filed Jun. 3, 2005.

Office Action mailed Oct. 24, 2008 for U.S. Appl. No. 12/001,618, filed Dec. 11, 2007.

Office Action mailed Jun. 3, 2008, for U.S. Appl. No. 12/008,473, filed Jan. 10, 2008.

Notice of Allowance mailed Oct. 15, 2008, for U.S. Appl. No. 12/008,473, filed Jan. 10, 2008.

Office Action mailed Mar. 21, 2008 for U.S. Appl. No. 11/634,354, filed Dec. 4, 2006.

Office Action mailed Sep. 16, 2008 for U.S. Appl. No. 11/634,354, filed Dec. 4, 2006.

Notice of Allowance mailed Mar. 20, 2009 for U.S. Appl. No. 11/634,354, filed Dec. 4, 2006.

Notice of Allowance mailed May 29, 2009 for U.S. Appl. No. 12/001,618, filed Dec. 11, 2007.

Office Action mailed Aug. 7, 2009 for U.S. Appl. No. 12/005,117, filed Dec. 20, 2007.

Supplemental Notice of Allowability mailed Jan. 23, 2008 for U.S. Appl. No. 11/145,159, filed Jun. 3, 2005.

Office Action mailed Sep. 3, 2003 for U.S. Appl. No. 09/972,411, filed Oct. 5, 2001.

Office Action mailed Feb. 23, 2004 for U.S. Appl. No. 09/972,411, filed Oct. 5, 2001.

Office Action mailed May 23, 2005 for U.S. Appl. No. 09/972,411, filed Oct. 5, 2001.

Notice of Allowance mailed Oct. 31, 2005 for U.S. Appl. No. 09/972,411, filed Oct. 5, 2001.

"Methylpyrrolidone" article from Wikipedia downloaded Aug. 24, 2012.

Airaksinen et al., Excipient selection can significantly affect solid-state phase transformation in formulation during wet granulation. *AAPS PharmSciTech 2005*, 6(2), E311-E322.

Alpert and Friedhoff, Paradoxical reaction to L-dopa in schizophrenic patients, *Am J Psychiatry*, 1978, 135(11), 1329-1332.

Bai, pGlu-L-Dopa-Pro: A tripeptide prodrug targeting the intestinal peptide transporter for absorption and tissue enzymes for conversion, Pharm. Res., 1995, 27(7), 1101-1104.

Berge et al., Pharmaceutical salts, *J. Pharm. Sci*, 1977, 66(1), 1-19.

Betarbet et al., Animal models of Parkinson's disease, *Bioessays*, 2002, 24(4), 308-318.

Bodor et al. Improved delivery through biological membranes. 4. Prodrugs of L-Dopa, *J. Med. Chem.*, 1977, 20(11), 1435-1445.

Boivin and Montplaisir, The effects of L-dopa on excessive daytime sleepiness in Narcolepsy, *Neurology*, 1991, 41, 1267-1269.

Bonelli and Wenning, Pharmacological management of Huntington's disease: an evidence-based review, *Current Pharmaceutical Design*, 2006, 12(21), 2701-2720.

Bruno and Bruno, Effects of L-dopa on pharmacological parkinsonism, *Acta Psychiatr Scand*, 1966, 42(3), 264-271.

(56) References Cited

OTHER PUBLICATIONS

Buchanan et al., Double blind trial of L-dopa in chronic schizophrenia, *Aust N Z J Psychiatry*, 1975, 9(4), 269-271.
Carboxylic Acid Derivatives and Nitriles, http://www.chem.uky.edu/Courses/che232/JEA!In/9.%20Esters etc.pdf, retrieved Mar. 24, 2010.
Cho et al., Dopamine neurons derived from embryonic stem cells efficiently induce behavioral recovery in a Parkinsonian rat model, *Biochemical ad Biophysical Research Communication*, 2006, 341(1), 6-12.
Coleman et al., A practical guide to polymer miscibility, *Polymer Reviews*, 1990, 31, 1187-1203.
Conti et al., Levodopa for idiopathic restless legs syndrome: evidence-based review, *Mot Disord*, 2007, 22(13), 1943-1951.
Cools, Dopaminergic modulation of cognitive function-implications for L-dopa treatment in Parkinson's disease, *Neuroscience Biobehavioral Rev*, 2006, 30, 1-23.
Cooper et al., L-Dopa esters as potential prodrugs: behavioural activity in experimental models of Parkinson's disease, *J. Pharma Pharmacology*, 1987, 39, 627-635.
Davey et al., Polymorphism in molecular crystals: stabilization of a metastable form by conformation mimicry, *J Am Chem Soc* 1997, 119(7), 1767-1772.
Di Stefano et al., Dimeric L-dopa derivatives as potential prodrugs, *Bioorganic & Medicinal Chem. Lett.*, 2001, 11, 1085-1088.
Doggrell, The therapeutic potential of dopamine modulators on the cardiovascular and renal systems, *Expert Opin. Investig., Drugs*, 2002, 11 (5), 631-644.
Durif et al., Worsening of levodopa-induced dyskinesias by motor and mental tasks, *Movement Disorders*, 1999, 14(2), 242-245.
During, Controlled release of dopamine from a polymeric brain implant: In vivo characterization, *Ann. Neurol.*, 1989, 25(4), 351-356.
Ebadi and Srinivasan, Pathogenesis, prevention and treatment of neuroleptic-induced movement disorders, *Pharmacological Reviews*, 1995, 47(4), 575-604.
Eltayb et al., Enhanced cortical dopamine output and antipsychotic-like effect of raclopride with adjunctive low-dose L-dopa. *Biol Psychiatry*, 2005, 58, 337-343.
Emborg, Evaluation of animal models of Parkinson's disease for neuroprotective strategies, *Journal of Neuroscience Methods*, 2004, 139(2), 121-143.
Fahn et al., Levodopa and the progression of Parkinson's disease, *N Engl J Med*, 2004, 351 (24), 2498-2508.
Faulkner et al., Gabapentin for the treatment of tremor, *The Annals of Pharmacotherapy*, 2003, 37(2), 282-286.
Fincher, Particle size of drugs and Its relationship to absorption and activity, *Journal of Pharmaceutical Sciences*, 1968, 57(11), 1825-1835.
Fix et al., A comparison of oral and rectal absorption of L-dopa ester in rats and mice, *Pharmaceutical Research*, 1990, 7(4), 384-387.
Fix et al., Short-chain alkyl esters of L-dopa as prodrugs for rectal absorption, *Pharmaceutical Research*, 1989, 6(6), 501-505.
Floel et al., Dopaminergic effects on encoding of a motor memory in chronic stroke, *Neurology*, 2005, 65(3), 472-474.
Floel et al., Levodopa increases memory encoding and dopamine release in the striatum in the elderly, *Neurobiology of Aging*, 2008, PMID 17098331.
Folstein et al., Mini-mental state. A practical method for grading the cognitive state of patients for the clinician, *J. Psychiat. Res.*, 1975, 12(3), 189-198.
Garcia-Borreguero et al., Treatment of restless legs syndrome with gabapentin: a double-blind, cross-over study, *Neurol*, 2002, 11(2), 1573-79.
Garzon-Aburbeh et al., A lymphotropic prodrug of L-Dopa: Synthesis, pharmacological properties, and pharmacokinetic behavior of 1,3-dihexadecanoyi-2-[(S)-2-amino-3-(3,4-dihydroxyphenyl)propanoyl]propane-1,2,3-triol, *J. Med. Chem.*, 1986, 29, 687-691.

Gelb et al., Diagnostic criteria for Parkinson disease, *Arch Neurol*, 1999, 56(1), 33-39.
Gerlach and Luhdorf, The effect of L-dopa on young patients with simple schizophrenia, treated with neuroleptic drugs, *Psychopharmacologia*, 1975, 44(1), 105-110.
Gibb et al., The relevance of the Lewy body to the pathogenesis of idiopathic Parkinson's disease, *J Neurol Neurosurg Psychiatry*, 1988, 51(6), 745-752.
Giovannoni et al., Bradykinesia akinesia incoordination test (Brain Test): An objective computerized assessment of upper limb motor function, *J Neurol Neurosurg Psychiatry*, 1999, 67, 624-629.
Hirsch et al., Animal models of Parkinson's disease in rodents induced by toxins: an update, *J. Neural Transm Suppl*, 2003, 65, 89-100.
Hisaka et al., Absorption of a novel product of L-Dopa, L-3-(3-hydroxy-4-pivaloyloxphenyl) alanine (NB-355), In vitro and In situ studies, *Drug Metabolism and Disposition*, 1990, 18(5), 621-625.
Hoes et al., The application of drug-polymer conjugates in chemotherapy, *Drug Carrier System*, 1989, 9, 57-100.
Hogl et al., Increased daytime sleepiness in Parkinson's disease: a questionnaire survey, *Movement Disorders*, 2003, 18(3), 319-323.
Howard et al., Intracerebral drug delivery in rats with lesion-induced memory deficits, *J Neurosurg*, 1989, 71, 105-112.
Inanaga et al., Double-blind controlled study of L-dopa therapy in schizophrenia, *Folia Psychiatr Neurol Jpn*, 1975, 29(2), 123-143.
Ishikura et al., Drug delivery to the brain. DOPA prodrugs based on a ring-closure reaction to quaternary thiazolium compounds, *Int'l. J. Pharmaceutics*, 1995, 116, 51-63.
Jankovic, Treatment of dystonia, *Lancet Neurol*, 2006, 5(10), 864-872.
Jaskiw and Popli, A meta-analysis of the response to chronic L-dopa in patients with schizophrenia: therapeutic and heuristic implications, *Psychopharmacology*, 2004, 171, 365-374.
Juncos et al., Levodopa methyl ester treatment of Parkinson's disease, *Neurology*, 1987, 37, 1242-1245.
Kay and Opler, L-dopa in the treatment of negative schizophrenic symptoms: a single-subject experimental study, *Int'l J Psychiatry Med*, 1985-86, 15(3), 293-298.
Kirk-Othmer Encyclopedia of Chemical Technology, John Wiley & Sons, Inc., pp. 95-147 (Aug. 2002).
Knecht et al., Levodopa: faster and better word learning in normal humans, *Ann. Neurol.*, 2004, 56(1), 20-26.
Kulisevsky, Role of dopamine in learning and memory: implications for the treatment of cognitive dysfunction in patients with Parkinson's disease, *Drugs Aging*, 2000, 16(5), 365-379.
Langer and Peppas, Chemical and physical structure of polymers as carriers for controlled release of bioactive agents: a review. *JMS-Rev. Macromol. Chem. Phys.* 1983, C23(1), 61-126.
Langer, Medical applications of controlled release, *Science*, 1983, C23(1), 61-126.
Langer, New methods of drug delivery, *Science*, 1990, 249, 1527-1533.
Leong and Langer., Polymeric controlled drug delivery, *Advanced Drug Delivery Reviews*, 1987, 1, 199-233.
Leppert et al., The effects of carbidopa dose and time and route of administration on systemic L-dopa levels in rats, *Pharmaceuticals Res.*, 1988, 5(9), 587-591.
Levy et al., Inhibition of calcification of bioprosthetic heart valves by local controlled-release diphosphonate, *Science*, 1985, 28, 190-192.
Lu and Yu, Dimensionless presentation for drug release from a coated pure drug bead: 2. Experiment, *Int. J. Pharm.*, 1994, 112, 117-124.
Ludatscher, Stable remission of tardive dyskinesia by L-dopa, *J Clin Psychopharm*, 1989, 9(1), 39-41.
Manson et al., an ambulatory dyskinesia monitor, *J. Neurol. Neurosurg. Psychiatry*, 2000, 68(2), 196-201.
Marrel et al., L-DOPA esters as potential prodrugs, *Eur. Journal Med. Chem. Chim. Ther.*, 1985, 5, 459-465.
Movement Disorder Society Task Force on Rating Scales for Parkinson's Disease. The Unified Parkinson's Disease Rating Scale (UPDRS): Status and Recommendations, *Movement Disorders*, 2003, 18(7), 738-750.
Nutt, Response to levodopa treatment in dopa-responsive dystonia, *Arch Neurol*, 2001, 58, 905-910.

(56) References Cited

OTHER PUBLICATIONS

O'Neill et al., LY503430: Pharmacology, pharmacokinetics, and effects in rodent models of Parkinson's disease, *CNS Drug Reviews*, 2005, 11(1), 77-96.

Olanow et al., Drug insight: continuous dopaminergic stimulation in the treatment of Parkinson's disease. *Nat Clin Pract Neurol* 2006, 2(7), 382-92.

Olson et al., Gabapentin for Parkinsonism: A double-blind, placebo-controlled, Crossover trial, *Am. J. Med.*, 1997, 102(1), 60-66.

Ondo and Jankovic, Restless legs syndrome: clinicoetiologic correlates, *Neurology*, 1996, 47(6), 1435-1441.

Orth and Tabrizi, Models of Parkinson's disease, *Movement Disorders*, 2003, 18(7), 729-737.

O'Suilleabhain and Dewey, Contributions of dopaminergic drugs and disease severity to daytime sleepiness in Parkinson disease, *Arch. Neurol*, 2002, 59, 986-989.

Paus et al., Sleep attacks, daytime sleepiness, and dopamine agonists in Parkinson's disease, *Movement Disorders*, 2003, 18(6), 659-667.

Racette and Perlmutter, Levodopa responsive parkinsonism in an adult with Huntington's Disease, *J Neurol Neurosurg Psychiatry*, 1998, 65(4), 577-579.

Rascol and Fabre, 2001, Dyskinesia: L-Dopa-induced and tardive dyskinesia, *Clinical Neuropharmacology*, 2001, 24(6), 313-323.

Rouhi, The right stuff, from research and development to the clinic, getting drug crystals right is full of pitfalls, *Science and Technology, C&E News*, Feb. 24, 2003, 32-35.

Saudek et al., A preliminary trail of the programmable implantable medication system for insulin delivery, *New England Journal of Medicine*, 1989, 321, 574-579.

Scheidtmann et al., Effect of levodopa in combination with physiotherapy on functional motor recovery after stroke: a prospective, randomized, double-blind study, *Lancet*, 2001, 358(9284), 787-790.

Schneider et al., Familial dopa-responsive cervical dystonia, *Neurology*, 2006, 66(4), 599-601.

Sefton, Implantable pumps, *CRC Crit. Rev. Biomed. Eng.*, 1987, 14(3), 201-240.

Silber, Sleep disorders, *Neurologic Clin*, 2001, 19(1), 173-186.

Soares and McGrath, The treatment of tardive dyskinesia—a systematic review and meta-analysis, *Schizophrenia Research*, 1999, 39, 1-16.

Staab et al., Control of polymorphism by 'tailor-made' polymeric crystallization auxiliaries. Preferential precipitation of a metastable polar form for second harmonic generation, *Adv Mater* 1990, 2(1), 40-43.

Tang et al., Synthesis and characterization of water-soluble and photostable L-dopa dendrimers, *Organic Letters*, 2006, 8(20), 4421-4424.

Tolwani et al., Experimental models of Parkinson's disease: Insights from many models, *Laboratory Animal Science*, 1999, 49(4), 363-371.

*Ullmann's Encyclopedia of Industrial Chemistry*, Wiley-VCH Verlag GmbH & Co. pp. 1-51 (2002).

Van Blercom et al., Effects of gabapentin on the motor response to levodopa: a double blind, placebo-controlled, crossover study in patients with complicated Parkinson disease, *Clin Neuropharmacol*, 2004, 27(3), 124-128.

Verma et al., Osmotically controlled oral drug delivery, *Drug Development and Industrial Pharmacy*, 2000, 26(7), 695-708.

Von Scheele, Levodopa in restless legs, *Lancet*, 1986, 2(8504), 426-427.

Wang et al, Synthesis and pharmacological activities of a novel tripeptide mimetic dopamine prodrug, *Bioorganic & Medicinal Chemistry Letters*, 1995, 5(19), 2195-2198.

Wang et al., Preparation and intestinal absorption of L-Dopa-D-phenylglycine, *J. Food and Drug Analysis*, 2002, 10(2), 81-87.

Wikstrom et al., Manipulating theophylline monohydrate formation during high-shear wet granulation through improved understanding of the role of pharmaceutical excipients, *Pharmaceutical Research* 2008, 25(4), 923-035.

International Search Report and Written opinion mailed Nov. 3, 2005, for PCT/US2005/019492 filed Jun. 3, 2005.

International Search Report and Written Opinion mailed Nov. 3, 2005, for PCT.US2005/019493 filed Jun. 3, 2005.

International Search Report and Written Opinion mailed Jul. 23, 2007, for PCT/US2006/046273 filed Apr. 12, 2006.

International Search Report and Written Opinion mailed Apr. 15, 2008, for PCT/US2007/026200 filed Dec. 20, 2007.

International Search Report and Written Opinion mailed May 14, 2008, for PCT/US2007/026271 filed Dec. 20, 2007.

International Search Report and Written Opinion mailed May 27, 2008, for PCT/US2007/078541 filed Sep. 14, 2007.

International Search Report, Written Opinion, and International Preliminary Report on Patentability mailed May 12, 2011, May 9, 2012, and May 19, 2012, respectively, for PCT/US2010/002937 filed Nov. 8, 2010.

International Search Report, Written Opinion, and International Preliminary Report on Patentability mailed Jul. 30, 2012, Apr. 20, 2011, and Apr. 26, 2011, respectively, for PCT/US2009/005698 filed Oct. 19, 2009.

Notice of Allowance mailed Dec. 16, 2009, for U.S. Appl. No. 12/005,117, filed Dec. 20, 2007.

Office Action mailed Jan. 25, 2010, for U.S. Appl. No. 12/005,120, filed Dec. 20, 2007.

Notice of Allowance mailed Jan. 25, 2010, for U.S. Appl. No. 12/005,120, filed Dec. 20, 2007.

Office Action mailed May 4, 2010, for U.S. Appl. No. 12/347,807, filed Dec. 31, 2008.

Office Action mailed Oct. 18, 2010, for U.S. Appl. No. 12/347,807, filed Dec. 31, 2008.

Notice of Allowance mailed Feb. 17, 2011, for U.S. Appl. No. 12/347,807, filed Dec. 31, 2008.

Office Action mailed Dec. 1, 2009, (later vacated) for U.S. Appl. No. 12/364,453, filed Feb. 2, 2009.

Office Action mailed Apr. 1, 2010, for U.S. Appl. No. 12/364,453, filed Feb. 2, 2009.

Office Action mailed Aug. 30, 2010, for U.S. Appl. No. 12/364,453, filed Feb. 2, 2009.

Notice of Allowance mailed Jan. 6, 2011, for U.S. Appl. No. 12/364,453, filed Feb. 2, 2009.

Office Action mailed Apr. 28, 2010, for U.S. Appl. No. 12/489,146, filed Jun. 22, 2009.

Notice of Allowance mailed Oct. 12, 2010, for U.S. Appl. No. 12/489,146, filed Jun. 22, 2009.

Office Action mailed Jun. 11, 2012, for U.S. Appl. No. 12/581,810, filed Oct. 19, 2009.

Office Action mailed Jun. 11, 2012, for U.S. Appl. No. 12/726,978, filed Mar. 18, 2010.

Notice of Allowance and Notice of Allowability mailed Aug. 14, 2012, for U.S. Appl. No. 12/726,978, filed Mar. 18, 2010.

Office Action mailed Apr. 30, 2012, for U.S. Appl. No. 12/904,960, filed Oct. 14, 2010.

Notice of Allowance and Notice of Allowability mailed Jul. 27, 2012, for U.S. Appl. No. 12/904,960, filed Oct. 14, 2010.

Office Action mailed Mar. 27, 2012, for U.S. Appl. No. 12/941,971, filed Nov. 8, 2010.

Office Action mailed May 18, 2012, for U.S. Appl. No. 13/010,419, filed Jan. 20, 2011.

Notice of Allowance mailed Feb. 7, 2012, for U.S. Appl. No. 13/010,419, filed Jan. 20, 2011.

Office Action mailed Sep. 22, 2011, for U.S. Appl. No. 13/095,101, filed Apr. 27, 2011.

Notice of Allowance mailed Dec. 27, 2011, for U.S. Appl. No. 13/095,101, filed Apr. 27, 2011.

Office Action mailed May 18, 2012, for U.S. Appl. No. 13/440,936, filed Apr. 5, 2012.

Office Action mailed Aug. 30, 2012, for U.S. Appl. No. 12/581,808, filed Oct. 19, 2009.

Non-Final Office Action mailed Nov. 23, 2012 for U.S. Appl. No. 13/473,503.

(56) References Cited

OTHER PUBLICATIONS

Notice of Allowance mailed Nov. 14, 2012 for U.S. Appl. No. 12/581,810.

Final Office Action mailed Sep. 27, 2012 for U.S. Appl. No. 12/941,971.

Final Office Action mailed Nov. 15, 2012 for U.S. Appl. No. 13/440,936.

* cited by examiner

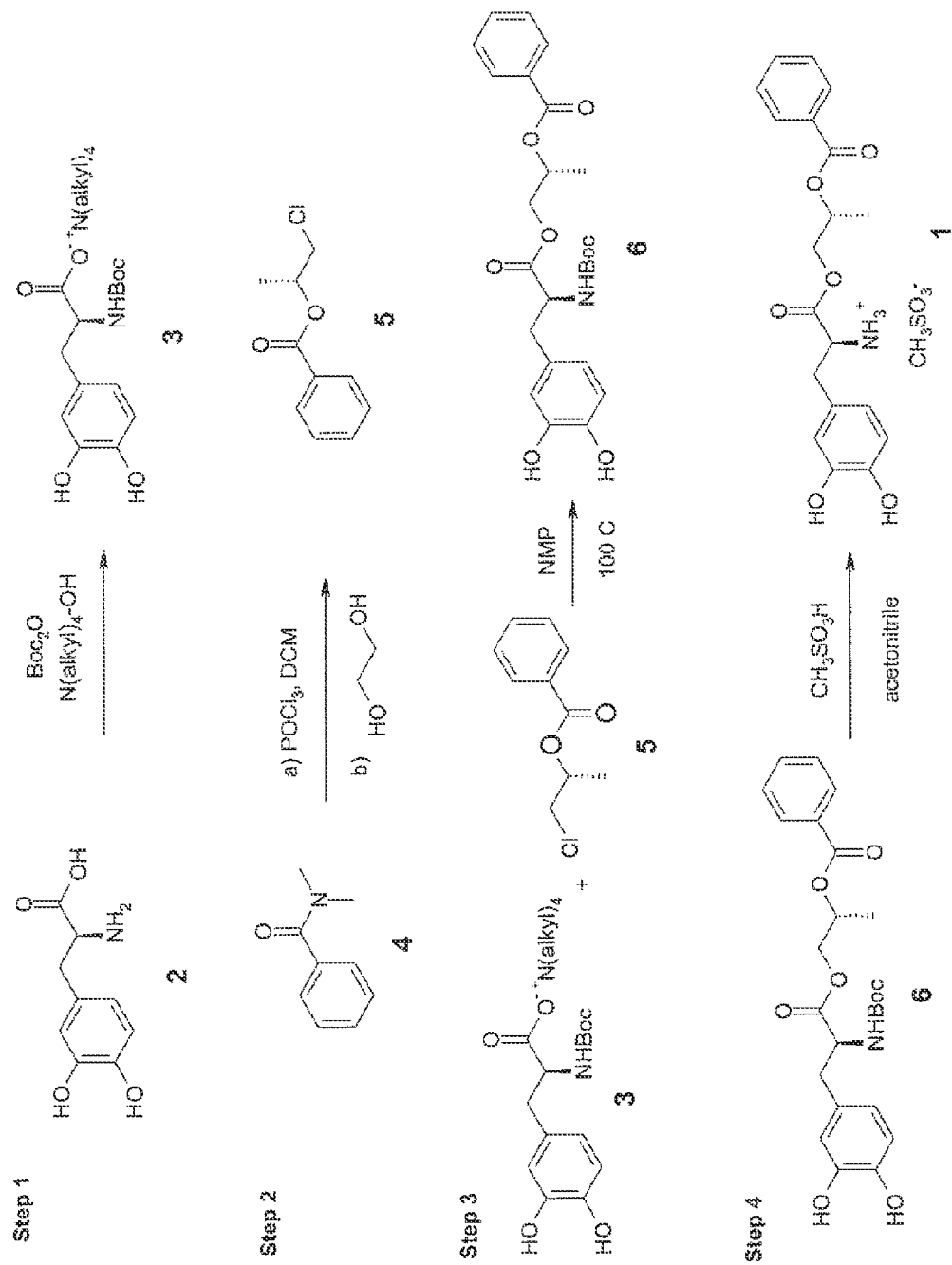

METHODS OF SYNTHESIZING A LEVODOPA ESTER PRODRUG

This application claims the benefit under 35 U.S.C. §119 (e) of U.S. Provisional Application No. 61/106,930 filed on Oct. 20, 2008, which is incorporated by reference in its entirety.

The present disclosure relates to methods of synthesizing a levodopa ester prodrug and synthetic intermediates thereof.

Parkinson's disease is a disabling, progressive illness that affects one in 1,000 people and generally occurs in people over the age of 50 years. Patients with Parkinson's disease have a deficiency of the neurotransmitter dopamine in the brain as a result of nigrostriatal pathway disruption caused by degeneration of the substantia nigra. Levodopa (L-dopa or L-3,4-dihydroxyphenylalanine), an immediate precursor of dopamine, is the most commonly prescribed drug for treatment of this disease.

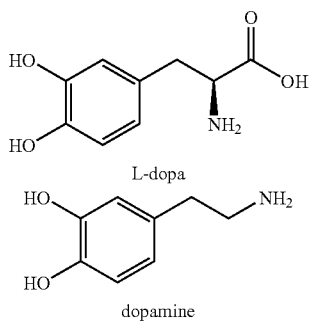

Following oral administration, levodopa is rapidly absorbed via an amino acid transporter present in the upper small intestine. Due to the narrow distribution of this transporter system, the window available for levodopa absorption is limited and the extent of absorption can depend on the rate at which the drug passes through the upper gastrointestinal tract.

Intestinal metabolism of levodopa is the major source of first pass loss of the drug. Approximately 35% of an administered dose of levodopa reaches the systemic circulation as intact levodopa after oral administration in patients (Sasahara, *J. Pharm. Sci* 1990, 69, 261). Once absorbed, levodopa is rapidly metabolized to dopamine by L-aromatic amino acid decarboxylase (AADC) enzymes in the peripheral tissues (e.g., intestines and liver). For this reason, levodopa is normally co-administered with a decarboxylase enzyme inhibitor such as carbidopa or benserazide. When administered with carbidopa, the plasma concentration of intact levodopa increases and thus more levodopa becomes available to be transported into the central nervous system where it is converted to dopamine. Carbidopa and benserazide do not cross the blood-brain barrier to a significant extent and therefore do not inhibit the required conversion of levodopa to dopamine in the brain.

The use of prodrugs of levodopa to improve the pharmacokinetics of levodopa has been proposed. Levodopa prodrugs designed to be absorbed in both the small and large intestines and methods of synthesizing such prodrugs have been described in Xiang et al., U.S. Pat. No. 7,323,585, U.S. Patent Application Publication No. 2008/0103200, U.S. Pat. No. 7,342,131, U.S. Pat. No. 7,534,813, U.S. Pat. No. 7,563,821, U.S. Patent Application Publication No. 2008/0171789, and U.S. Patent Application Publication No. 2008/0214663, each of which is incorporated by reference in its entirety. These levodopa prodrugs can achieve an oral bioavailability of levodopa that is at least two times greater than the oral bioavailability of levodopa when orally administered on an equivalent molar basis. More specifically, Xiang et al., U.S. Pat. No. 7,342,131 disclose the compound (2R)-2-phenylcarbonyloxypropyl(2S)-2-amino-3-(3,4-dihydroxyphenyl)propanoate hydrochloride in an amorphous or crystalline form (see Example 8 of Xiang et al.), and Xiang et al., U.S. Pat. No. 7,563,821 discloses the (2R)-2-phenylcarbonyloxypropyl(2S)-2-amino-3-(3,4-dihydroxyphenyl)propanoate, methanesulfonate salt. The prodrugs described by Xiang et al. can be efficaciously incorporated into sustained release formulations to provide sustained systemic exposure to levodopa upon oral administration to a patient.

Xiang et al., U.S. Pat. No. 7,144,877 describe the synthesis of acyloxyalkyl prodrugs of L-dopa by reacting Boc-protected L-dopa with a halide in the presence of a base such as an alkali metal bicarbonate or carbonate followed by hydrolysis of the Boc protecting group under acidic conditions to provide the corresponding acyloxyalkyl L-dopa prodrug. Xiang et al., U.S. Pat. No. 7,144,877 also describe an alternate route of synthesizing L-dopa prodrugs via coupling of Boc-protected L-dopa with an alcohol intermediate under standard couple conditions followed by removal of the Boc protecting group. Xiang et al., U.S. Patent Application Publication No. 2008/0171789 and U.S. Patent Application Publication No. 2008/0214663 disclose the synthesis of acyloxyalkyl L-dopa prodrugs from diols, from 2-hydroxyethyl halides, or from ethylene dihalides.

Alternative methods of synthesizing (2R)-2-phenylcarbonyloxypropyl(2S)-2-amino-3-(3,4-dihydroxyphenyl)propanoate, methanesulfonate and other pharmaceutically acceptable salts of (2R)-2-phenylcarbonyloxypropyl(2S)-2-amino-3-(3,4-dihydroxyphenyl)propanoate that are synthetically robust and provide the desired levodopa prodrugs with high yield and reasonable purity are disclosed.

In a first aspect, methods of synthesizing (2R)-2-phenylcarbonyloxypropyl(2S)-2-amino-3-(3,4-dihydroxyphenyl)propanoate are disclosed comprising reacting 3-(3,4-dihydroxyphenyl)-(2S)-[(tert-butoxy)carbonylamino]propanoate tetraalkylammonium salt with (1R)-2-halogen-isopropyl benzoate in a first solvent to provide (2R)-2-phenylcarbonyloxypropyl(2S)-3-(3,4-dihydroxyphenyl)-2-[(tert-butoxy)carbonylamino]propanoate.

In a second aspect, methods of synthesizing 3-(3,4-dihydroxyphenyl)-(2S)-[(tert-butoxy)carbonylamino]propanoate tetraalkylammonium salt are disclosed comprising reacting (2S)-2-amino-3-(3,4-dihydroxyphenyl)propanoic acid with di-tert-butyl dicarbonate and tetraalkylammonium hydroxide in a mixture of alcohol and water at a temperature ranging from about 20° C. to about 60° C. in an inert atmosphere to provide 3-(3,4-dihydroxyphenyl)-(2S)-[(tert-butoxy)carbonylamino]propanoate tetraalkylammonium salt.

In a third aspect, the compound 3-(3,4-dihydroxyphenyl)-(2S)-[(tert-butoxy)carbonylamino]propanoate tetraalkylammonium salt is disclosed.

BRIEF DESCRIPTION OF THE DRAWINGS

Those skilled in the art will understand that the drawings described herein are for illustration purposes only. The drawings are not intended to limit the scope of the present disclosure.

FIG. 1 shows steps in the synthesis of (2R)-2-phenylcarbonyloxypropyl(2S)-2-amino-3-(3,4-dihydroxyphenyl)propanoate, methanesulfonate and synthetic intermediates wherein X is halogen.

Reference is now made in detail to certain embodiments of compounds, compositions, and methods. The disclosed embodiments are not intended to be limiting of the claims. To the contrary, the claims are intended to cover all alternatives, modifications, and equivalents.

Methods provided by the present disclosure include methods of synthesizing (2R)-2-phenylcarbonyloxypropyl(2S)-2-amino-3-(3,4-dihydroxyphenyl)propanoate, methanesulfonate 1 (also referred to as (2R)-2-phenylcarbonyloxypropyl(2S)-2-amino-3-(3,4-dihydroxyphenyl)propanoate mesylate);

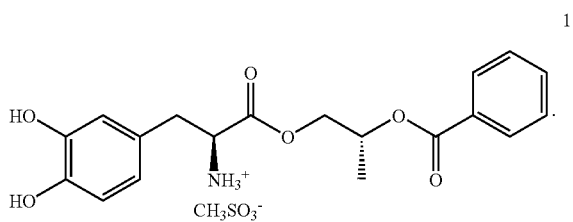

and other pharmaceutically acceptable salts of (2R)-2-phenylcarbonyloxypropyl(2S)-2-amino-3-(3,4-dihydroxyphenyl)propanoate.

In certain embodiments methods of synthesizing (2R)-2-phenylcarbonyloxypropyl(2S)-2-amino-3-(3,4-dihydroxyphenyl)propanoate are disclosed comprising reacting 3-(3,4-dihydroxyphenyl)-(2S)-[(tert-butoxy)carbonylamino]propanoate tetraalkylammonium salt with (1R)-2-halogen-isopropyl benzoate in a first solvent to provide (2R)-2-phenylcarbonyloxypropyl(2S)-3-(3,4-dihydroxyphenyl)-2-[(tert-butoxy)carbonylamino]propanoate.

In certain embodiments, the tetraalkylammonium salt is chosen from the tetramethyl ammonium salt, the tetraethylammonium salt, the tetrapropylammonium salt, and the tetrabutylammonium salt. In certain embodiments, the tetraalkylammonium salt is the tetraethylammoniumm salt, and in certain embodiments is the tetrabutylammonium salt.

In certain embodiments, the first solvent is chosen from N-methyl-2-pyrrolidone, dimethyl formamide, dimethyl acetamide, dimethylsulfoxide, 1,4-dioxane, and a mixture of any of the foregoing.

In certain embodiments, (1R)-2-halogen-isopropyl benzoate is (1R)-2-chloro-isopropyl benzoate.

In certain embodiments, the first solvent is N-methyl-2-pyrrolidone.

In certain embodiments, reacting 3-(3,4-dihydroxyphenyl)-(2S)-[(tert-butoxy)carbonylamino]propanoate tetraalkylammonium salt with (1R)-2-chloro-isopropyl benzoate in a first solvent to provide (2R)-2-phenylcarbonyloxypropyl(2S)-3-(3,4-dihydroxyphenyl)-2-[(tert-butoxy)carbonylamino]propanoate is carried out at a temperature ranging from about 70° C. to about 80° C.

In certain embodiments, the method further comprises reacting (2R)-2-phenylcarbonyloxypropyl(2S)-3-(3,4-dihydroxyphenyl)-2-[(tert-butoxy)carbonylamino]propanoate with an acid in a second solvent to provide the corresponding (2R)-2-phenylcarbonyloxypropyl(2S)-2-amino-3-(3,4-dihydroxyphenyl)propanoate salt.

In certain embodiments, the method further comprises reacting (2R)-2-phenylcarbonyloxypropyl(2S)-3-(3,4-dihydroxyphenyl)-2-[(tert-butoxy)carbonylamino]propanoate with methanesulfonic acid in a second solvent to provide (2R)-2-phenylcarbonyloxypropyl(2S)-2-amino-3-(3,4-dihydroxyphenyl)propanoate, methanesulfonate.

In certain embodiments, the second solvent is chosen from acetonitrile, acetone, ethyl acetate, toluene, isopropanol, dichloromethane, and a mixture of any of the foregoing.

In certain embodiments the second solvent is chosen from acetonitrile and dichlormethane. In certain embodiments, the second solvent is acetonitrile In certain embodiments, reacting (2R)-2-phenylcarbonyloxypropyl(2S)-3-(3,4-dihydroxyphenyl)-2-[(tert-butoxy)carbonylamino]propanoate with methanesulfonic acid in a second solvent to provide (2R)-2-phenylcarbonyloxypropyl(2S)-2-amino-3-(3,4-dihydroxyphenyl)propanoate, methanesulfonate is carried out at a temperature ranging from about 30° C. to about 50° C.

In certain embodiments, the method further comprises cooling the second solvent to form crystalline (2R)-2-phenylcarbonyloxypropyl(2S)-2-amino-3-(3,4-dihydroxyphenyl)propanoate, methanesulfonate.

In certain embodiments, the method further comprises seeding the cooled second solvent with crystalline (2R)-2-phenylcarbonyloxypropyl(2S)-2-amino-3-(3,4-dihydroxyphenyl)propanoate, methanesulfonate.

In certain embodiments, the method further comprises recrystallizing (2R)-2-phenylcarbonyloxypropyl(2S)-2-amino-3-(3,4-dihydroxyphenyl)propanoate, methanesulfonate.

In certain embodiments, recrystallizing (2R)-2-phenylcarbonyloxypropyl(2S)-2-amino-3-(3,4-dihydroxyphenyl)propanoate, methanesulfonate comprises dissolving (2R)-2-phenylcarbonyloxypropyl(2S)-2-amino-3-(3,4-dihydroxyphenyl)propanoate, methanesulfonate in a third solvent; and cooling the third solvent to form crystalline (2R)-2-phenylcarbonyloxypropyl(2S)-2-amino-3-(3,4-dihydroxyphenyl)propanoate, methanesulfonate.

In certain embodiments, the third solvent is chosen from acetonitrile, acetone, ethyl acetate, water, and a mixture of any of the foregoing.

In certain embodiments, the third solvent is chosen from acetonitrile and a mixture of acetonitrile and water.

In certain embodiments, (1R)-2-halogen-isopropyl benzoate is prepared comprising reacting N,N-dimethylbenzamide with phosphoryl halogen in a fourth solvent to provide dimethylbenzamide Vilsmeier salt; and reacting dimethylbenzamide Vilsmeier salt with (2R)-propane-1,2-diol to provide (1R)-2-halogen-isopropyl benzoate.

In certain embodiments, phosphoryl halogen is phosphoryl chloride and (1R)-2-halogen-isopropyl benzoate is (1R)-2-chloro-isopropyl benzoate.

In certain embodiments wherein phosphoryl halogen is phosphoryl chloride and (1R)-2-halogen-isopropyl benzoate is (1R)-2-chloro-isopropyl benzoate, reacting N,N-dimethylbenzamide with phosphoryl halogen to provide dimethylbenzamide Vilsmeier salt is carried out at a temperature ranging from about 70° C. to about 95° C.

In certain embodiments, the fourth solvent is dichloromethane.

In certain embodiments, wherein phosphoryl halogen is phosphoryl chloride and (1R)-2-halogen-isopropyl benzoate is (1R)-2-chloro-isopropyl benzoate reacting dimethylbenzamide Vilsmeier salt with (2R)-propane-1,2-diol to provide (1R)-2-chloro-isopropyl benzoate is carried out at a temperature ranging from about 0° C. to about 10° C.

In certain embodiments, 3-(3,4-dihydroxyphenyl)-(2S)-[(tert-butoxy)carbonylamino]propanoate tetraalkylammonium salt is prepared comprising reacting (2S)-2-amino-3-(3,4-dihydroxyphenyl)propanoic acid with di-tert-butyl dicarbonate and tetraalkylammonium hydroxide to provide 3-(3,4-dihydroxyphenyl)-(2S)-[(tert-butoxy)carbonylamino]propanoate tetraalkylammonium salt.

In certain embodiments, reacting (2S)-2-amino-3-(3,4-dihydroxyphenyl)propanoic acid with di-tert-butyl dicarbonate and tetraalkylammonium hydroxide to provide 3-(3,4-dihydroxyphenyl)-(2S)-[(tert-butoxy)carbonylamino]propanoate tetraalkylammonium salt is carried out in a mixture of an alcohol and water.

In certain embodiments, the mixture of an alcohol and water comprises from about 0%-b.v. to about 4%-b.v. water.

In certain embodiments, the alcohol is chosen from methanol, ethanol, isopropanol, and a mixture of any of the foregoing.

In certain embodiments, reacting (2S)-2-amino-3-(3,4-dihydroxyphenyl)propanoic acid with di-tert-butyl dicarbonate to provide 3-(3,4-dihydroxyphenyl)-(2S)-[(tert-butoxy)carbonylamino]propanoate tetraalkylammonium salt is carried out at a temperature ranging from about 30° C. to about 50° C.

Steps in the synthesis of (2R)-2-phenylcarbonyloxypropyl(2S)-2-amino-3-(3,4-dihydroxyphenyl)propanoate methanesulfonate 1 and synthetic intermediates are shown in FIG. 1.

In a first reaction step, Boc-L-dopa tetraalkylammonium salt 3 (3-(3,4-dihydroxyphenyl)-(2S)-[(tert-butoxy)carbonylamino]propanoate tetraalkyl ammonium salt) can be prepared by reacting L-dopa 2 with di-tert-butyl dicarbonate (Boc-anhydride, $Boc_2O$) and tetraalkylammonium hydroxide in an alcohol/water mixture at a temperature ranging from about 20° C. to about 60° C. in an inert atmosphere. The amount of water in the alcohol/water mixture can range from about 0%-b.v. to about 5%-b.v., from about 1%-b.v. to about 4%-b.v., from about 1%-b.v. to about 3%-b.v., and in certain embodiments, is about 2%-b.v. In certain embodiments the alcohol can be chosen from methanol, ethanol, isopropanol, and a mixture of any of the foregoing, and in certain embodiments, the alcohol is methanol. Alternatively, the reaction can be carried out in a dipolar aprotic solvent such as N-methyl-2-pyrrolione (NMP), dimethyl formamide (DMF), dimethylacetamide (DMA), dimethyl sulfoxide (DMSO), or a mixture of any of the foregoing. In certain embodiments the temperature of the reaction can range from about 30° C. to about 60° C., from about 35° C. to about 55° C., and in certain embodiments, at a temperature of about 40° C.

(1R)-2-Chloro-isopropyl benzoate 5 can be prepared by reacting N,N-dimethylbenzamide with a phosphoryl halogen such as phosphoryl chloride (phosphorous oxychloride II, $POCl_3$) in an organic solvent such as dichloromethane under an inert atmosphere to provide the (chlorophenylmethylene) dimethylamide chloride salt (Vilsmeier salt) intermediate, which can then be reacted with (R)-1,2-propanediol to provide (1R)-2-chloro-isopropyl benzoate 5. Formation of the iminium intermediate can be carried out at a temperature ranging from about 65° C. to about 105° C. from about 75° C. to about 95° C., and in certain embodiments, at a temperature of about 85° C. The diol coupling reaction can be carried out by adding the diol to the reaction mixture while maintaining the temperature from about 0° C. to about 10° C., after which the reaction mixture can be warmed to a temperature ranging from about 15° C. to about 35° C., and in certain embodiments, to about 25° C., and allowed to react until the Vilsmeier salt intermediate is consumed.

In a third step, 3-(3,4-dihydroxyphenyl)-(2S)-[(tert-butoxy)carbonylamino]propanoate tetraalkylammonium salt 3 can be reacted under an inert atmosphere with (1R)-2-chloro-isopropyl benzoate 5 to provide (2R)-2-phenylcarbonyloxypropyl(2S)-3-(3,4-dihydroxyphenyl)-2-[(tert-butoxy)carbonylamino]propanoate 6.

The reaction can be carried out in a dipolar aprotic solvent such as N-methyl-2-pyrrolione (NMP), dimethyl formamide (DMF), dimethylacetamide (DMA), dimethyl sulfoxide (DMSO), 1,4-dioxane, or a mixture of any of the foregoing. In certain embodiments, the solvent is N-methyl-2-pyrrolione (NMP). The temperature of the reaction can range from about 50° C. to about 120° C., from about 70° C. to about 80° C., and in certain embodiments, at a temperature of about 75° C.

In a fourth step, (2R)-2-phenylcarbonyloxypropyl(2S)-3-(3,4-dihydroxyphenyl)-2-[(tert-butoxy)carbonylamino]propanoate 6 can be reacted with methanesulfonic acid to provide (2R)-2-phenylcarbonyloxypropyl(2S)-2-amino-3-(3,4-dihydroxyphenyl)propanoate, methanesulfonate 1. The reaction can be carried out in a solvent chosen from isopropanol, acetonitrile, toluene, dichloromethane, and a mixture of any of the foregoing. In certain embodiments, the solvent is chosen from acetonitrile and dichloromethane. The reaction can be carried out at a temperature ranging from about 20° C. to about 60° C., from about 30° C. to about 50° C., and in certain embodiments, at a temperature of about 40° C. (2R)-2-Phenylcarbonyloxypropyl(2S)-2-amino-3-(3,4-dihydroxyphenyl)propanoate, methanesulfonate 1 can precipitate from the solution as a crystalline solid, i.e., crystalline (2R)-2-phenylcarbonyloxypropyl(2S)-2-amino-3-(3,4-dihydroxyphenyl)propanoate, methanesulfonate 1.

Using appropriate reaction conditions such as those described for the synthesis of (2R)-2-phenylcarbonyloxypropyl(2S)-2-amino-3-(3,4-dihydroxyphenyl)propanoate, methanesulfonate 1 in the fourth step, other salts of (2R)-2-phenylcarbonyloxypropyl(2S)-2-amino-3-(3,4-dihydroxyphenyl)propanoate can be prepared. For example, methanesulfonic acid can be replaced with a different acid and reacted using an appropriate solvent and at an appropriate temperature to provide the corresponding (2R)-2-phenylcarbonyloxypropyl(2S)-2-amino-3-(3,4-dihydroxyphenyl)propanoate salt. In certain embodiments, the acid is chosen from hydrochloric acid, sulfuric acid, phosphoric acid, methanesulfonic acid, ethanesulfonic acid, benzenesulfonic acid, and 4-toluenesulfonic acid, to produce the corresponding pharmaceutically acceptable salt of (2R)-2-phenylcarbonyloxypropyl(2S)-2-amino-3-(3,4-dihydroxyphenyl)propanoate.

"Pharmaceutically acceptable" refers to approved or approvable by a regulatory agency of the Federal or a state government or listed in the U.S. Pharmacopoeia or other generally recognized pharmacopoeia for use in animals, and more particularly in humans. Pharmaceutically acceptable salt refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt, and in certain embodiments, the sodium salt. In certain embodiments, a pharmaceutically acceptable salt is the methanesulfonic acid salt.

(2R)-2-Phenylcarbonyloxypropyl(2S)-2-amino-3-(3,4-dihydroxyphenyl)propanoate, methanesulfonate 1 can be recrystallized by first dissolving the compound in a solvent chosen from acetonitrile, isopropanol, toluene, water, and a mixture of any of the foregoing and a trace amount of water. In certain embodiments, the solvent is chosen from acetonitrile and a mixture of acetonitrile and water. The solution can then be filtered and then slowly cooled to precipitate crystalline (2R)-2-phenylcarbonyloxypropyl(2S)-2-amino-3-(3,4-dihydroxyphenyl)propanoate, methanesulfonate 1. Using the methods disclosed herein, (2R)-2-phenylcarbonyloxypropyl(2S)-2-amino-3-(3,4-dihydroxyphenyl)propanoate, methanesulfonate 1 can be synthesized with an overall yield of about 20% to about 25%, and with purity greater than about 95% purity, greater than about 97% purity, and in certain embodiments, greater than about 98% purity.

(2R)-2-Phenylcarbonyloxypropyl(2S)-2-amino-3-(3,4-dihydroxyphenyl)propanoate methanesulfonate 1 may exist in several tautomeric forms. Accordingly, all possible tautomeric forms of (2R)-2-phenylcarbonyloxypropyl(2S)-2-amino-3-(3,4-dihydroxyphenyl)propanoate methanesulfonate are encompassed unless otherwise specified. All isotopically labeled forms of (2R)-2-phenylcarbonyloxypropyl(2S)-2-amino-3-(3,4-dihydroxyphenyl)propanoate methanesulfonate are also encompassed unless otherwise specified. Examples of isotopes that may be incorporated into (2R)-2-phenylcarbonyloxypropyl(2S)-2-amino-3-(3,4-dihydroxyphenyl)propanoate methanesulfonate include, but are not limited to, $^2$H, $^3$H, $^{11}$C, $^{13}$C, $^{14}$C, $^{15}$N, $^{18}$O, and $^{17}$O.

In certain embodiments, (2R)-2-phenylcarbonyloxypropyl(2S)-2-amino-3-(3,4-dihydroxyphenyl)propanoate methanesulfonate 1 is crystalline. In certain embodiments, an X-ray powder diffraction pattern of crystalline (2R)-2-phenylcarbonyloxypropyl(2S)-2-amino-3-(3,4-dihydroxyphenyl)propanoate methanesulfonate exhibits characteristic scattering angles °2θ at least at 4.7±0.2°, 5.0±0.2°, 8.5±0.2°, 9.6±0.2°, 13.6±0.2°, 15.0±0.2°, 17.0±0.2°, 17.4±0.2°, 17.7±0.2°, 19.1±0.2°, 19.5±0.2°, 20.0±0.2°, 20.4±0.2°, 21.1±0.2°, 22.3±0.2°, 22.9±0.2°, 23.1±0.2°, 23.3±0.2°, 24.3±0.2°, 25.0±0.2°, 25.3±0.2°, 25.7±0.2°, 25.8±0.2°, 26.9±0.2°, 27.3±0.2°, 28.2±0.2°, 30.1±0.2°, 30.5±0.2°, 32.0±0.2°, 33.8±0.2°, 34.3±0.2°, 37.6±0.2°, and 38.4±0.2° using Cu—Kα radiation. In certain embodiments, an X-ray powder diffraction pattern of crystalline (2R)-2-phenylcarbonyloxypropyl(2S)-2-amino-3-(3,4-dihydroxyphenyl)propanoate methanesulfonate exhibits characteristic scattering angles °2θ at least at 5.0±0.2°, 8.5±0.2°, 13.6±0.2°, 15.0±0.2°, 17.0±0.2°, 17.7±0.2°, 20.4±0.2°, 21.1±0.2°, 25.0±0.2°, 25.8±0.2°, 28.2±0.2°, 30.1±0.2°, and 37.6±0.2° using Cu—Kα radiation. One skilled in the art will recognize that slight variations in the observed °2θ diffraction angles can be expected based on, for example, the specific diffractometer employed, the analyst, and the sample preparation technique. Greater variation can be expected for the relative peak intensities. Comparison of diffraction patterns can be based primarily on observed °2θ diffraction angles with lesser importance attributed to relative peak intensities.

In certain embodiments, crystalline (2R)-2-phenylcarbonyloxypropyl(2S)-2-amino-3-(3,4-dihydroxyphenyl)propanoate methanesulfonate exhibits a melting point ranging from about 157° C. to about 162° C.

In certain embodiments, crystalline (2R)-2-phenylcarbonyloxypropyl(2S)-2-amino-3-(3,4-dihydroxyphenyl)propanoate methanesulfonate is characterized by a differential scanning calorimetry (DSC) thermogram having an endothermic peak at about 164.5° C., and in certain embodiments at about 164.5±2.5° C.

In certain embodiments, crystalline (2R)-2-phenylcarbonyloxypropyl(2S)-2-amino-3-(3,4-dihydroxyphenyl)propanoate methanesulfonate is stable, e.g., does not absorb moisture and/or convert to another isomorphic form under pharmaceutical processing and/or storage conditions.

Levodopa prodrugs are precursors of dopamine. Thus, (2R)-2-phenylcarbonyloxypropyl(2S)-2-amino-3-(3,4-dihydroxyphenyl)propanoate methanesulfonate synthesized using methods provided by the present disclosure may be administered to a patient suffering from any disease or disorder for which the parent drug, levodopa, is known or hereafter determined to be therapeutically effective. (2R)-2-Phenylcarbonyloxypropyl(2S)-2-amino-3-(3,4-dihydroxyphenyl)propanoate methanesulfonate may be administered to a patient, such as a human, to treat a disease or disorder such as Parkinson's disease. The methods comprise administering to a patient in need of such treatment a therapeutically effective amount of (2R)-2-phenylcarbonyloxypropyl(2S)-2-amino-3-(3,4-dihydroxyphenyl)propanoate methanesulfonate. In therapeutic methods provided by the present disclosure, a therapeutically effective amount of (2R)-2-phenylcarbonyloxypropyl(2S)-2-amino-3-(3,4-dihydroxyphenyl)propanoate methanesulfonate may be administered to a patient suffering from a disease such as Parkinson's disease, depression, attention deficit disorder, schizophrenia, manic depression, a cognitive impairment disorder, restless legs syndrome, a periodic limb movement disorder, tardive dyskinesia, Huntington's disease, Tourette's syndrome, hypertension, an addictive disorder, congestive heart failure, or excessive daytime sleepiness.

As used herein, the abbreviation "b.v." or "bv" means "by volume". Particularly, when referencing a mixture of more than one fluids, the term % b.v. reflects the percentage of one fluid in the total volume. As a non-limiting example a mixture of methanol and water that is 10% b.v. water comprises 10 units of water and 90 units of methanol.

EXAMPLES

The following examples describe in detail the preparation of (2R)-2-phenylcarbonyloxypropyl(2S)-2-amino-3-(3,4-dihydroxyphenyl)propanoate, methanesulfonate and synthetic intermediates using methods disclosed herein. It will be apparent to those skilled in the art that many modifications, both to materials and methods, may be practiced without departing from the scope of the disclosure.

Example 1

Synthesis of (2R)-2-Phenylcarbonyloxypropyl(2S)-2-amino-3-(3,4-dihydroxyphenyl)propanoate, Methanesulfonate (1)

Step 1: Boc-L-Dopa tetrabutylammonium salt (3)

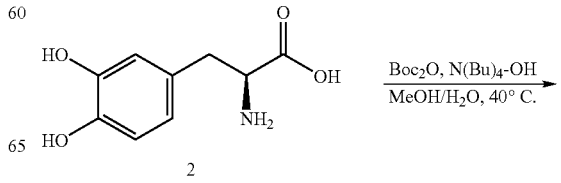

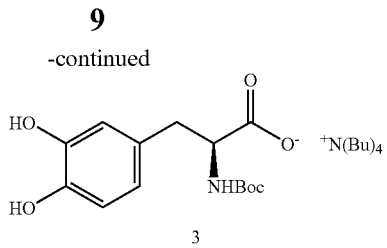

3

To a 10-liter jacketed pilot plant reaction vessel equipped with an overhead stirrer, a digital temperature monitor with a temperature probe, a reflux condenser, and a nitrogen line, 986 g (5 mol) of L-Dopa 2 was added followed by 2,183 g (10 mol) of di-tert-butyl dicarbonate anhydride (Boc$_2$O) and 1 L of methanol (MeOH) under a nitrogen atmosphere. The resulting suspension was warmed to 40° C. A tetrabutylammonium hydroxide solution (1,000 mL of a 1 M solution in methanol, 1 mol), water (36 mL, 2 mol), and methanol (100 mL) were added in five 1.136 L aliquots (a total of 5 mol of TBA-OH, 10 mL, H$_2$O and 500 mL MeOH) over 30 minutes. After 5 hours, an additional 273 g (1.25 mol) of Boc$_2$O anhydride was added. The reaction mixture was stirred at 40° C. for 21 hrs.

Possible traces of unreacted L-Dopa were filtered off under nitrogen by vacuum filtration into a 20 L rotary evaporator flask using a gas dispersion tube with a coarse, glass frit for the filtration. The filtrate was concentrated under vacuum to an oil. The oil was diluted under nitrogen with ethyl acetate (EtOAc) (16.5 L). The milky mixture was stirred at room temperature for 40 hrs. During this time the product precipitated out as a white to off-white solid. The resulting mixture was further cooled using an ice-bath for 1 h. The product was collected by centrifugation and washed with ethyl acetate (EtOAc) (500 mL). The resulting white solid was dried in a vacuum oven at 40° C. for 20 hrs to provide 2479.2 g (92.2% yield) of Boc-L-dopa tetrabutylammonium salt 3. $^1$H NMR (400 MHz, CD$_3$CN): δ 0.95 (t, J=7.2 Hz, 12H), 1.33 (m, 8H), 1.42 (s, 9H), 1.57 (m, 8H), 2.88 (m, 2H), 3.05 (m, 8H), 3.93 (m, 1H), 5.40 (d, J=6.4 Hz, 1H), 6.33 (dd, J=7.8, 1.6 Hz, 1H), 6.47 (d, J=8.0 Hz, 1H), 6.60 (d, J=2.0 Hz, 1H).

Step 2: (1R)-2-Chloro-isopropyl Benzoate (5)

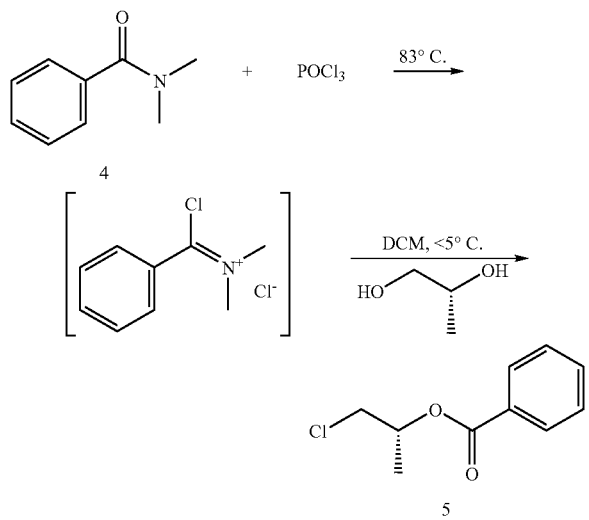

To a 10 liter mini pilot plant was added 3133 g (21.04 mol) of N,N-dimethylbenzamide 4 followed by 3,624 g (23.7 mol) of phosphorus oxychloride. The resulting suspension was stirred under nitrogen and slowly warmed. The suspension cleared as the reaction was warmed. When the temperature reached 40° C. an exotherm occurred which brought the temperature up to 83° C. over a few minutes. The reaction was stirred at 83° C.

The formation of the intermediate Vilsmeier salt was complete in 15 minutes at 85° C. as determined by $^1$H-NMR. The reaction was stirred an additional 1.5 hrs. The resulting clear, yellow solution was transferred to another 10 liter pilot plant and cooled to 0° C., and then diluted with two liters of dichloromethane (DCM). Two (2) kg (26.3 mole) of (R)-1,2-propanediol was slowly added to the reaction mixture over 2 hours while maintaining the temperature between 0° C. and 10° C.

Upon completion of the diol addition, the external cooling was removed and the reaction mixture was warmed to room temperature and stirred for 16 hours.

Two (2) L of the reaction mixture was added to 2 L of ice cold water with vigorous stirring to thoroughly mix the two phases. The phases were then separated and the process repeated with the remaining reaction mixture (total 5 times). The combined organic phases were washed with brine (500 mL), dried with anhydrous sodium sulfate (Na$_2$SO$_4$), and concentrated to yield 3,850 g of a dark-orange oil. The oil was dissolved in heptane (8 L) and the organic phase washed with water (2 L) followed by brine (3×500 mL). The product was dried over anhydrous sodium sulfate (Na$_2$SO$_4$) and concentrated to provide 3,590 g of crude (1R)-2-chloro-isopropyl benzoate 5 as a dark, yellow-orange oil. $^1$H NMR (400 MHz, CDCl$_3$): δ 1.47 (d, J=6.4 Hz, 3H), 3.71 (m, 2H), 5.35 (m, 1H), 7.42 (m, 2H), 7.54 (t, J=7.6 Hz, 1H), 8.06 (d, J=7.2 Hz, 2H).

Step 3: (2R)-2-Phenylcarbonyloxypropyl (2S)-3-(3,4-dihydroxyphenyl)-2-[(tert-butoxy)carbonylamino]propanoate (6)

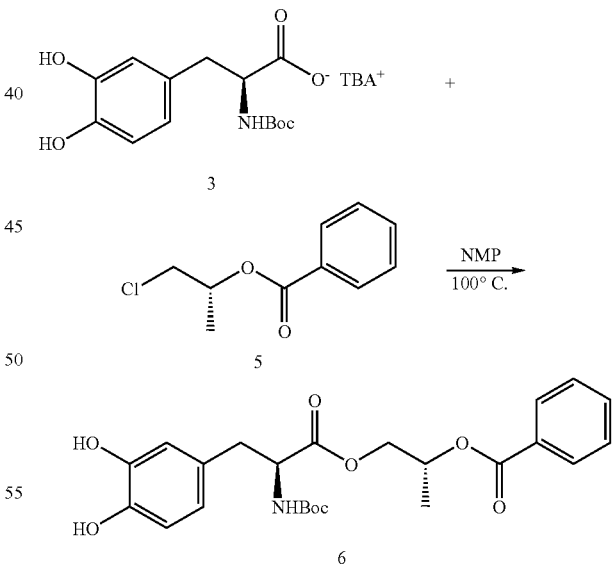

Boc-L-dopa tetrabutylammonium salt 3 (2000 g, 3.7 mol), N-methylpyrrolidone (3700 mL) and un-distilled chlorobenzoate (1R)-2-chloro-isopropyl benzoate 5 (1171 g, 5.91 mol) from Step 2 was added to a 10 L mini pilot plant. The resulting dark-green slurry was heated to 100° C. for 18 hours under nitrogen, which resulted in a clear, dark-yellow solution.

After 18 hrs a sample of the reaction mixture was diluted with methyl tert-butyl ether (MTBE) and extracted 3 times with water. This work-up efficiently extracted Boc-L-dopa tetrabutylammonium salt 3 into the water phase. The organic phase was evaporated and the progress of the reaction determined using $^1$H NMR in CDCl$_3$.

After cooling, the crude reaction mixture was divided in half and each part worked-up separately. The dark reaction mixture was transferred to a 22 L separatory funnel containing cold water (5 L). This mixture was then extracted with methyl tert-butyl ether (MTBE, 3 L). This sequence was repeated with the second half of the crude reaction mixture. The organic phases of both work-ups were combined and washed with water (2 L), brine (2 L), and dried over anhydrous sodium sulfate (Na$_2$SO$_4$). The solvent was evaporated and the resulting oil was triturated twice with heptane (2 L each) in a 45° C. water bath. The warm heptane phase was decanted. The resulting oil was further dried under vacuum for 2 hrs to provide 1,500 g of crude (2R)-2-phenylcarbonyloxypropyl(2S)-3-(3,4-dihydroxyphenyl)-2-[(tert-butoxy)carbonylamino]propanoate 6 as a dark oil. NMR (CDCl$_3$) δ 1.4 (3h, d), 1.45 (9H, s), 2.95 (2H, d), 4.25 (1H, t), 4.2-4.6 (4H, m), 5.4 (1H, br s), 6.42 (2H, m), 6.7 (1H, d), 7.43 (2H, m), 7.6 (1H, m), 8.03 (2H, d); MS 482.19 (M+Na)$^+$, 458.14 (M-H)$^-$.

Step 4: (2R)-2-Phenylcarbonyloxypropyl (2S)-2-amino-3-(3,4-dihydroxyphenyl)propanoate, methanesulfonate (1)

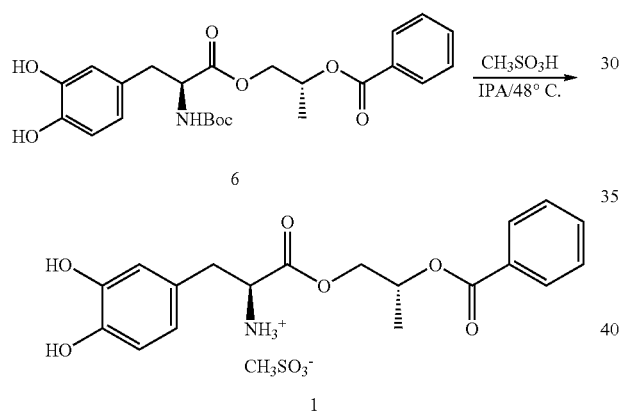

Crude (2R)-2-phenylcarbonyloxypropyl(2S)-3-(3,4-dihydroxyphenyl)-2-[(tert-butoxy)carbonylamino]propanoate 6 (1500 g) from Step 3 was dissolved in isopropanol (7,400 mL). Methanesulfonic acid (376 g, 3.9 mol) was added, which caused the temperature to rise to 49° C. The mixture was stirred for 16 hours at 45° C.

The reaction mixture was transferred to a 5-gallon plastic bucket and cooled to 5° C. for 7 hrs. The crystallized material was filtered using a basket centrifuge and washed with several aliquots of ethyl acetate (EtOAc) (ca. 4 L). The solid was dried under vacuum at 50° C. for 18 hrs to provide 723 g of (2R)-2-phenylcarbonyloxypropyl(2S)-2-amino-3-(3,4-dihydroxyphenyl)propanoate, methanesulfonate 1 as a white to off-white solid. Purity: 98.5% w/w; 97.6% AUC. M.p. 156-158° C. DSC: endotherm at 161.54° C. $^1$H NMR (400 MHz, CD$_3$OD): δ 1.40 (d, J=6.4 Hz, 3H), 2.70 (s, 3H), 2.98 (dd, J=14.6, 7.8 Hz, 1H), 3.10 (dd, J=14.4, 5.6 Hz, 1H), 4.24 (dd, J=7.8, 5.8 Hz, 1H), 4.38 (dd, J=12.0, 6.8 Hz, 1H), 4.52 (dd, J=311.8, 3.4 Hz, 1H), 5.40 (dq, J=6.4, 3.2 Hz, 1H), 6.52 (dd, J=7.8, 2.2 Hz, 1H), 6.69 (m, 2H), 7.48 (m, 2H), 7.60 (m, 1H), 8.01 (m, 2H).

Example 2

Alternate Step 3: (2R)-2-Phenylcarbonyloxypropyl (2S)-3-(3,4-dihydroxyphenyl)-2-[(tert-butoxy)carbonylamino]propanoate (6)

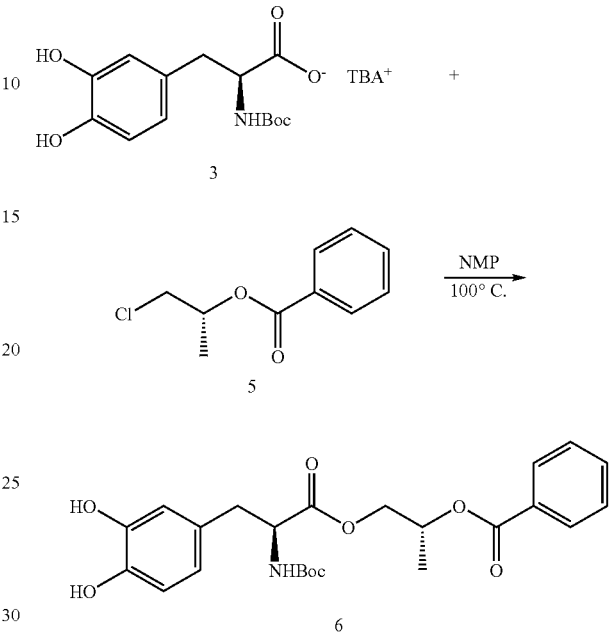

Boc-Dopa TBA salt 3 (50 g, 93 mmol), bicarbonate-washed (1R)-2-chloroisopropyl benzoate 5 (20 g, 100 mmol), and N-methylpyrrolidinone (NMP) (100 mL) were added to a 250 mL round bottom flask. The mixture was stirred under a nitrogen atmosphere and heated in an oil bath at 100° C. After ca. 72 hrs the reaction was cooled to room temperature, diluted with tert-butyl methylether (MTBE) (1 L), and washed twice with deionized water (2 L, then 1 L). The organic phase was separated, dried over anhydrous sodium sulfate (Na$_2$SO$_4$), filtered, and concentrated under reduced pressure to provide 35 g (76 mmol) of (2R)-2-phenylcarbonyloxypropyl(2S)-3-(3,4-dihydroxyphenyl)-2-[(tert-butoxy)carbonylamino]propanoate 6 as a tan, viscous oil.

Alternate Step 4: (2R)-2-Phenylcarbonyloxypropyl (2S)-2-amino-3-(3,4-dihydroxyphenyl)propanoate, methanesulfonate (1)

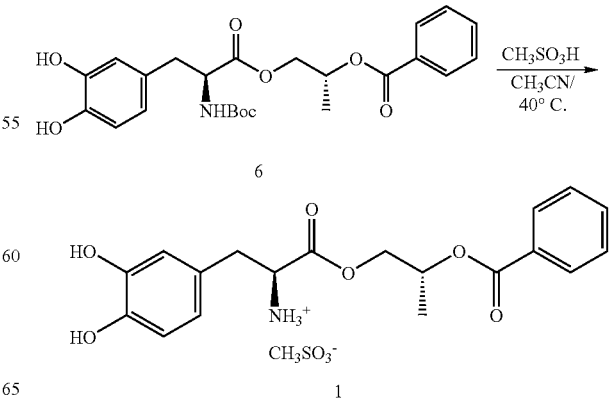

Example 3

(2R)-2-Phenylcarbonyloxypropyl(2S)-3-(3,4-dihydroxyphenyl)-2-[(tert-butoxy)carbonylamino]propanoate 6 (35 g, 76 mmol) was dissolved in acetonitrile (CH$_3$CN) (150 mL). The mixture was stirred in a water bath at 40° C., followed by the addition of methanesulfonic acid (7.3 g, 4.93 mL). At 26° C. the reaction was seeded with 50 mg of (2R)-2-phenylcarbonyloxypropyl(2S)-2-amino-3-(3,4-dihydroxyphenyl)propanoate, methanesulfonate 1, followed by further cooling to 21° C. with formation of a thick slurry. The material was diluted with acetonitrile (CH$_3$CN) (150 mL) and cooled in a freezer at −20° C. for 16 hrs. The precipitate was then collected by filtration and washed with ethyl acetate (EtOAc) (500 mL). The off-white solid (19.3 g, 42 mmol) was dried under vacuum to provide 19.3 g (42 mmol) of (2R)-2-phenylcarbonyloxypropyl(2S)-2-amino-3-(3,4-dihydroxyphenyl)propanoate, methanesulfonate 1. $^1$H NMR (DMSO-d$_6$) δ 1.30 (3h, d), 2.29 (3H, s), 2.90 (2H, d), 4.25 (1H, t), 4.31 (1H, dd), 4.39 (1H, dd), 5.25 (1H, m), 6.41 (1H, dd), 6.57 (1H, d), 6.59 (1H, d), 7.52 (2H, m), 7.63 (1H, m), 7.93 (2H, m), 8.26 (3H, br s), 8.85 (1H, s), 8.89 (1H, s); mp 163-164° C. Purity (HPLC): 96.1 w/w % purity, and 95.0% purity by AUC.

Example 4

Recrystallization of (2R)-2-Phenylcarbonyloxypropyl(2S)-2-amino-3-(3,4-dihydroxyphenyl)propanoate, methanesulfonate (1)

(2R)-2-Phenylcarbonyloxypropyl(2S)-2-amino-3-(3,4-dihydroxyphenyl)propanoate, methanesulfonate 1 (19.3 g, 42 mmol) was suspended in acetonitrile (CH$_3$CN) (400 mL) and heated in a water bath at 80° C. Deionized water (4 mL) was then added causing most of the material to dissolve. The solution was filtered through a sintered glass funnel to remove undissolved solids. The solution was stirred and slowly cooled at a rate of 15° C./hour. At about 60° C. the solution began to crystallize. When the temperature reached 21° C. the solid was collected by filtration and washed with acetonitrile (CH$_3$CN) (100 mL) and tert-butyl methyl ether (MTBE) (100 mL). The solid was then dried under vacuum for 24 hrs to provide 14.7 g (32.3 mmol) of crystalline (2R)-2-phenylcarbonyloxypropyl(2S)-2-amino-3-(3,4-dihydroxyphenyl)propanoate, methanesulfonate 1 as an off-white solid.

Example 5

Synthesis of (2R)-2-Phenylcarbonyloxypropyl(2S)-2-amino-3-(3,4-dihydroxyphenyl)propanoate, Methanesulfonate (1)

Step 1: Boc-L-Dopa tetrabutylammonium salt (3)

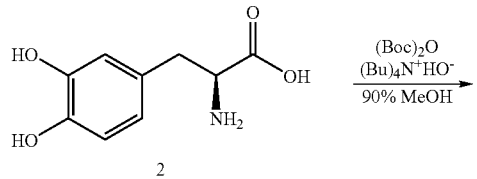

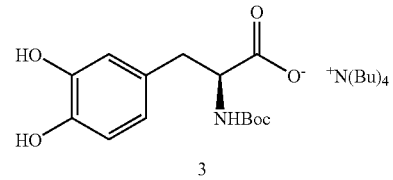

L-Dopa 2 (19 kg, 96 moles) and Boc-anhydride (42.2 kg, 193 moles) in 0.8 parts methanol (15 kg) were charged to a 380 L glass-lined reactor. The reactor was then charged with water (3.6 kg, 0.19 parts) in a 1 M tetrabutylammonium hydroxide methanol solution (80 kg, 4.21 parts) at 40° C., rinsing forwards with methanol (4 kg, 0.2 parts). The temperature of the mixture was adjusted to 45° C. to a maximum 50° C. and agitated for ca. 5 hours. Boc anhydride (5.3 kg, 24 moles, Boc$_2$O) was charged and rinsed forward with methanol (4 kg, 0.2 parts). The reaction was monitored until one of the two intermediates disappeared or became faint as determined by TLC and not more than 2% by HPLC. After filtration, the filtrate was concentrated to 4 volume parts (76 L) and the residue was co-evaporated with ethyl acetate (EtOAc) (95 kg, 15 parts) until 4 parts volume (76 L). After adjusting the temperature to 22° C. (19-25° C.), ethyl acetate (EtOAc) (287 kg, 15 parts) was charged and the resultant mixture was agitated at 22° C. (19-25° C.) for a minimum of 6 hours, cooled to 3° C. (0-6° C.) and agitated at 3° C. (0-6° C.) for a minimum of 10 hours. The product was filtered and washed with ethyl acetate (EtOAc) (19 kg, 1 part). The wet cake was slurry washed in ethyl acetate (EtOAc) (95 kg, 5 parts) at 22° C. (19-25° C.) for a minimum of 6 hrs. After filtration and washing with ethyl acetate (EtOAc) (19 kg, 1 part), the product, Boc-L-dopa tetrabutylammonium salt 3, was dried at a maximum temperature of 55° C. until LOD was max. 1%. The yield was 40.6 kg (78%) after correction for LOD and purity (minimum 97 A %).

Step 2: (1R)-2-Chloro-isopropyl Benzoate (5)

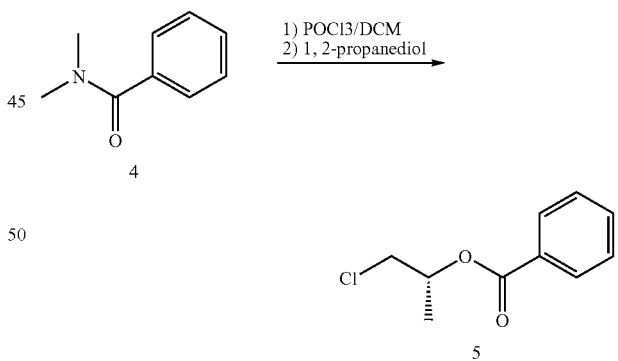

A 380 L glass lined reactor was conditioned with dichloromethane to remove moisture. Dimethylbenzamide 4 (30 kg, 201 moles) and dichloromethane (63 kg, 2.1 parts) were charged to the reactor and warmed to 40-45° C. Phosphorous oxychloride (34.5 kg, 225 mole, 1.15 parts) was charged over ca. 2 hrs while reflux was maintained using a metering pump. The line and pump were rinsed forward with dichloromethane (17 kg, 0.55 parts). The mixture was agitated under reflux for ca. 4 hrs. The temperature was adjusted to ca. 5° C. (R)-1,2-propanediol (19.2 kg, 252 moles, 0.64 parts) was diluted with dichloromethane (26 kg, 0.85 parts) in a drum. The solution was added to the reactor over ca. 5.4 hours (min 4 hrs), maintaining a temperature of 2° C. to 10° C. (target 5° C.). The pump and lines were rinsed forward with dichloromethane (3 kg, 0.1 parts). The temperature of the reactor was adjusted to 22° C. over ca. 80 min (minimum 60 min). The reactants were agitated for ca. 11 hrs. The reaction mixture was then transferred to a 760 L glass-lined reactor containing water (150 kg, 5 parts), maintaining a temperature from 19° C. to 40° C. until the exotherm ceased (ca. 1 hr). The temperature of the reactor was adjusted to 22° C. and the contents agitated for another ca. 1 hr. The phases were separated. The aqueous layer was back-extracted with dichloromethane (51 kg, 1.7 parts). The organic layers were combined and washed with an aqueous sodium bicarbonate solution (water 110 kg, 3.65 parts and sodium bicarbonate 5.7 kg, 0.19 parts). The pH of the organic layer (ph≥7) and aqueous layer (pH≥9) were determined, and then the phases were separated. Sodium sulfate (9 kg, 0.3 parts) was added to the organic layer and the mixture agitated at 22° C. for ca. 60 min. The slurry was filtered to remove sodium sulfate (Na$_2$SO$_4$) (125 L pressure Nutsche) to provide a final stock solution (269 kg, TDS 11.3%, HPLC 91.3 A %). The reactor and filtrate were rinsed forward with dichloromethane (30 kg, 1 part) to provide a rinse solution containing (1R)-2-chloro-isopropyl benzoate 5 (25.5 kg, TDS 1.5%, HPLC 91.7 A %) (yield 70.9%).

Step 3: (2R)-2-phenylcarbonyloxypropyl (2S)-3-(3,4-dihydroxyphenyl)-2-[(tert-butoxy)carbonylamino]propanoate (6)

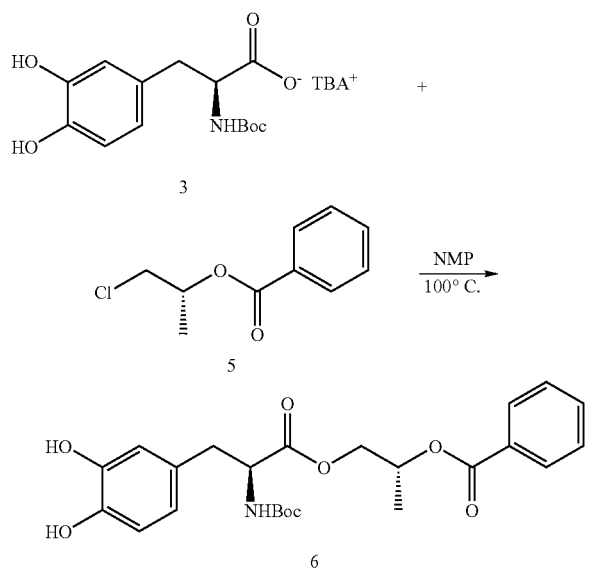

A 380 L glass lined reactor was conditioned with dichloromethane to remove moisture. The (1R)-2-chloro-isopropyl benzoate 5 stock solution from Step 2 (205 kg, TDS 11.3%, 21.3 kg, 107.2 moles, 1.5 eq) was charged to the reactor and concentrated until distillation stopped, at a maximum W/G temperature of 50° C. Vacuum was then applied at maximum W/G temperature of 40° C., and concentration was continued for ca. 1 hour. A dichloromethane content of 1.6% was achieved.

1-Methyl-2-pyrrolidone (NMP) (77.7 kg, 2.0 parts) was charged to the reactor and the temperature was adjusted to 22° C. Boc-Dopa TBA 3 (38.7 kg, 1.0 part, 71.83 moles) was charged to the reactor via a hand hole, followed by potassium phosphate, dibasic (12.4 kg, 71.19 moles, 0.32 parts, 1 eq).

The temperature was adjusted to 100° C. (97-103° C.), and reacted until the reaction was complete as determined by HPLC (20-36 hr). After the reaction was complete, the temperature was adjusted to 22° C. (19-25° C.) and the solids filtered off (pressure Nutsche). The reaction and filter were forward rinsed with 1-methyl-2-pyrrolidone (NMP) (39.2 kg, 1.0 part). The filtrate and rinse were transferred to a 1,900 L glass-lined reactor and the organics washed three times to partially remove un-reacted starting material. Heptane (126 kg, 3.25 parts) was charged to the reactor, followed by tetrahydrofuran (9.7 kg, 0.25 parts), and the contents were agitated at 22° C. for ca. 1 hour. The layers were allowed to separate for ca. 60 minutes.

The lower organic layer containing 1-methyl-2-pyrrolidone (NMP) and (2R)-2-phenylcarbonyloxypropyl(2S)-3-(3, 4-dihydroxyphenyl)-2-[(tert-butoxy)carbonylamino]propanoate 6 was transferred to a 380 L glass-lined reactor. The remaining organics in the 1,900 L reactor were jogged for ca. 10 seconds, every 15 minutes for ca. 60 minutes, to loosen any product containing organics from the reactor walls, which were then drained to the 380 L reactor. The organics were returned to the 1,900 L reactor and washed twice with THF/heptane. After the final THF/heptane wash, the organic layer was returned to the 1900 L reactor. Methyl tert-butyl ether (MTBE) (39 kg, 1 part) was charged to the 380 L reactor and agitated. Water (39 kg, 1 part) was added to the 380 L reactor and agitated for 15 minutes. The 380 L reactor, the pump, and the lines were rinsed forward to the 1,900 L reactor. Methyl tert-butyl ether (MTBE) (116 kg, 3 parts) was added to the 1,900 L reactor, followed by water (368 kg, 9.5 parts) at a maximum temperature of 30° C. The addition of water was exothermic. The temperature was adjusted to 22° C. (19-25° C.) and the reactants moderately agitated for ca. 1 hour. Agitation was stopped and the layers allowed to separate for ca. 60 minutes.

The lower aqueous layer was transferred to 200 L polyethylene drums using a 30 L separatory funnel and the upper organic layer was transferred to the 380 L reactor. The aqueous layer was returned to the 1900 L reactor and methyl tert-butyl ether (MTBE) (77 kg, 2 parts) was added. The temperature was adjusted to 22° C. (19-25° C.) and the mixture moderately agitated for ca. 1 h. Agitation was stopped, and the layers allowed to separate for ca. 60 minutes. The lower aqueous layer was discharged using a 30 L separatory funnel. The organic product was transferred to the 1,900 L reactor and combined with the organic methyl tert-butyl ether (MTBE) layer in the 1,900 L reactor. The 380 L reactor and the pump lines were rinsed forward with ca. 20 kg methyl tert-butyl ether (MTBE) to the 1,900 L reactor. A solution of sodium bicarbonate (21.3 kg, 0.55 parts) in water (271 kg, 7.0 parts) was added to the organic layer while maintaining the temperature of the reactor at less than 30° C. The temperature was adjusted to 22° C. (19-25° C.) and moderately agitated for ca. 1 hour.

Agitation was stopped, and the layers were allowed to separate for ca. 60 minutes. The target pH parameter, for the organic layer was pH≥7, and the target for the aqueous layer was pH≥9. The aqueous layer was drained to drums until the emulsion became visible. Diatomaceous earth (10 kg) was added to the reactor and the mixture agitated for ca. 15-30 minutes. The mixture was filtered through a pressure Nutsche and the filtrate drained to clean polyethylene drums. The filtrate was then transferred to the 1900 L reactor. Water (77.4 kg, 2 parts) was added to the reactor and moderately agitated for ca. 1 hour. Agitation was stopped and the layers allowed to separate for ca. 60 minutes. The aqueous layer was then drained into polyethylene drums. Sodium sulfate (Na$_2$SO$_4$)

(39.2 kg, 1 part) was added and the mixture agitated at 22° C. for ca. 60 min. The slurry was filtered to remove sodium sulfate (Na$_2$SO$_4$) using a 125 L pressure Nutsche to provide a solution containing (2R)-2-phenylcarbonyloxypropyl(2S)-3-(3,4-dihydroxyphenyl)-2-[(tert-butoxy)carbonylamino]propanoate 6 (214 kg methyl tert-butyl ether (MTBE) stock solution, TDS 12.4%, HPLC 51.4 A %, 13.5 kg (2R)-2-phenylcarbonyloxypropyl(2S)-3-(3,4-dihydroxyphenyl)-2-[(tert-butoxy)carbonylamino]propanoate 6). The reactor, pump lines, and filter were rinsed forward with MTBE (50 kg, 2 parts) and drummed off separately (98.4 kg, TDS 0.83%%, HPLC 47.9 A %, 0.39 kg, a total of 13.9 kg (2R)-2-phenylcarbonyloxypropyl(2S)-3-(3,4-dihydroxyphenyl)-2-[(tert-butoxy)carbonylamino]propanoate 6, 42.4% yield. 35-65% expected).

Step 4: (2R)-2-phenylcarbonyloxypropyl (2S)-2-amino-3-(3,4-dihydroxyphenyl)propanoate, methanesulfonate (1)

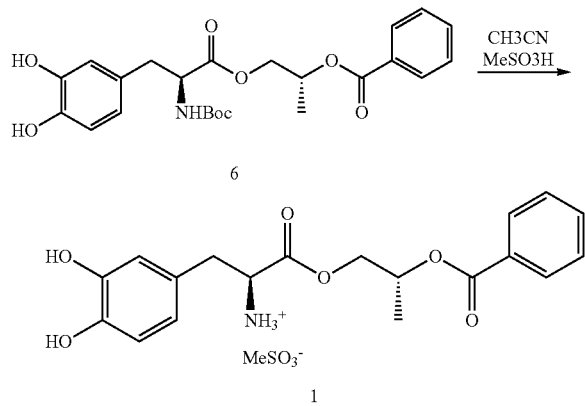

The solution of (2R)-2-phenylcarbonyloxypropyl(2S)-3-(3,4-dihydroxyphenyl)-2-[(tert-butoxy)carbonylamino]propanoate 6 from Step 3 was added to a 570 L glass-lined reactor and rinsed with methyl tert-butyl ether (MTBE) (312.4 kg, 13.9 kg). The contents were concentrated under vacuum at a maximum W/G temperature of 40° C. until distillation stopped. Acetonitrile (CH$_3$CN) (116 kg, 3.0 parts) was charged to the reactor and the vacuum distillation repeated until distillation ended. Additional acetonitrile (CH$_3$CN) (112 kg, 2.9 parts) was charged to the reactor and the temperature was adjusted to 40° C. (39-41° C.). Methanesulfonic acid (MeSO$_3$H) (6.97 kg, 0.18 parts) was charged to the reactor while maintaining the temperature at 40° C. (35-45° C.). The pump and lines were rinsed forward with acetonitrile (CH$_3$CN) (3.9 kg, 0.1 part). The reaction was complete after two hrs (2-6 hrs expected) at 40° C. (35-45° C.) as determined by high pressure liquid chromatography (HPLC). The temperature of the mixture was adjusted to 22° C. (19-25° C.) and agitated for 32 hrs. The crude product was collected by centrifugation, the reactor, lines, and filter cake rinsed forward with acetonitrile (CH$_3$CN) (38.7 kg, 1 part) and spun as dry as possible to provide a wet filter cake (10.9 kg). A portion of the wet filter cake (8.0 kg) was transferred to a 570 L glass-lined reactor. Acetonitrile (CH$_3$CN) (278 kg, 10 parts) was charged to the reactor, the contents agitated, and the temperature adjusted to reflux (80-82° C.). Water (2.8 kg, 0.1 parts) was charged to the reactor, maintaining the temperature at 80-82° C. The suspension became a clear solution. The mixture was agitated at 80-82° C. for ca. 30 minutes. The solution was then cooled over 6 hrs to 22° C. (19-25° C.) with a slurry forming at 60° C. The slurry was held at 22° C. (19-25° C.) for an additional 2 hrs. The product, (2R)-2-phenylcarbonyloxypropyl(2S)-2-amino-3-(3,4-dihydroxyphenyl)propanoate, methanesulfonate 1, was collected by centrifugation and the reactor, lines, and filter cake were rinsed with 3 portions of methyl tert-butyl ether (MTBE) (30 kg each) and spun dry. The product was dried at a maximum temperature of 55° C. until LOD was ≤0.5% and acetonitrile is ≤400 ppm as determined by gas chromatography (GC) to provide 5.4 kg of (2R)-2-phenylcarbonyloxypropyl(2S)-2-amino-3-(3,4-dihydroxyphenyl)propanoate, methanesulfonate 1.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A method of synthesizing (2R)-2-phenylcarbonyloxypropyl(2S)-2-amino-3-(3,4-dihydroxyphenyl)propanoate comprising reacting 3-(3,4-dihydroxyphenyl)-(2S)-[tert-butoxy)carbonylamino]propanoate tetraalkylammonium salt with (1R)-2-chloro-isopropyl benzoate in N-methyl-2-pyrrolidone to provide (2R)-2-phenylcarbonyloxypropyl(2S)-3-(3,4-dihydroxyphenyl)-2-[(tert-butoxy)carbonylamino]propanoate.

2. The method of claim 1, wherein reacting 3-(3,4-dihydroxyphenyl)-(2S)-[(tert-butoxy)carbonylamino]propanoate tetraalkylammonium salt with (1R)-2-chloro-isopropyl benzoate in N-methyl-2-pyrrolidone to provide (2R)-2-phenylcarbonyloxypropyl(2S)-3-(3,4-dihydroxyphenyl)-2-[(tert-butoxy)carbonylamino]propanoate is carried out at a temperature ranging from about 70° C. to about 80° C.

3. The method of claim 1, comprising reacting (2R)-2-phenylcarbonyloxypropyl(2S)-3-(3,4-dihydroxyphenyl)-2-[(tert-butoxy)carbonylamino]propanoate with an acid in a second solvent to provide the corresponding (2R)-2-phenylcarbonyloxypropyl(2S)-2-amino-3-(3,4-dihydroxyphenyl)propanoate salt.

4. The method of claim 1, comprising reacting (2R)-2-phenylcarbonyloxypropyl(2S)-3-(3,4-dihydroxyphenyl)-2-[(tert-butoxy)carbonylamino]propanoate with methanesulfonic acid in a second solvent to provide (2R)-2-phenylcarbonyloxypropyl(2S)-2-amino-3-(3,4-dihydroxyphenyl)propanoate, methanesulfonate.

5. The method of claim 4, wherein the second solvent is chosen from acetonitrile, acetone, ethyl acetate, toluene, isopropanol, dichloromethane, and a mixture of any of the foregoing.

6. The method of claim 5, wherein the second solvent is chosen from acetonitrile and dichloromethane.

7. The method of claim 4, wherein reacting (2R)-2-phenylcarbonyloxypropyl(2S)-3-(3,4-dihydroxyphenyl)-2-[(tert-butoxy)carbonylamino]propanoate with methanesulfonic acid in a second solvent to provide (2R)-2-phenylcarbonyloxypropyl(2S)-2-amino-3-(3,4-dihydroxyphenyl)propanoate, methanesulfonate is carried out at a temperature ranging from about 30° C. to about 50° C.

8. The method of claim 4, comprising cooling the second solvent to form crystalline (2R)-2-phenylcarbonyloxypropyl(2S)-2-amino-3-(3,4-dihydroxyphenyl)propanoate, methanesulfonate.

9. The method of claim 8, comprising seeding the cooled second solvent with crystalline (2R)-2-phenylcarbonyloxypropyl(2S)-2-amino-3-(3,4-dihydroxyphenyl)propanoate, methanesulfonate.

10. The method of claim 8, comprising recrystallizing (2R)-2-phenylcarbonyloxypropyl(2S)-2-amino-3-(3,4-dihydroxyphenyl)propanoate, methanesulfonate.

11. The method of claim 10, wherein recrystallizing (2R)-2-phenylcarbonyloxypropyl(2S)-2-amino-3-(3,4-dihydroxyphenyl)propanoate, methanesulfonate comprises:
   dissolving (2R)-2-phenylcarbonyloxypropyl(2S)-2-amino-3-(3,4-dihydroxyphenyl)propanoate, methanesulfonate in a third solvent; and
   cooling the third solvent to form crystalline (2R)-2-phenylcarbonyloxypropyl(2S)-2-amino-3-(3,4-dihydroxyphenyl)propanoate, methanesulfonate.

12. The method of claim 11, wherein the third solvent is chosen from acetonitrile, acetone, ethyl acetate, water, and a mixture of any of the foregoing.

13. The method of claim 12, wherein the third solvent is chosen from acetonitrile and a mixture of acetonitrile and water.

14. The method of claim 1, wherein (1R)-2-chloro-isopropyl benzoate is prepared comprising:
   reacting N,N-dimethylbenzamide with phosphoryl halogen in a fourth solvent to provide dimethylbenzamide Vilsmeier salt; and
   reacting dimethylbenzamide Vilsmeier salt with (2R)-propane-1,2-diol to provide (1R)-2-chloro-isopropyl benzoate.

15. The method of claim 14, wherein phosphoryl halogen is phosphoryl chloride.

16. The method of claim 15, wherein reacting N,N-dimethylbenzamide with phosphoryl chloride to provide dimethylbenzamide Vilsmeier salt is carried out at a temperature ranging from about 70° C. to about 95° C.

17. The method of claim 15, wherein the fourth solvent is dichloromethane.

18. The method of claim 15, wherein reacting dimethylbenzamide Vilsmeier salt with (2R)-propane-1,2-diol to provide (1R)-2-chloro-isopropyl benzoate is carried out at a temperature ranging from about 0° C. to about 10° C.

19. The method of claim 1, wherein 3-(3,4-dihydroxyphenyl)-(2S)-[(tert-butoxy)carbonylamino]propanoate tetraalkylammonium salt is prepared comprising:
   reacting (2S)-2-amino-3-(3,4-dihydroxyphenyl)propanoic acid with di-tert-butyl dicarbonate and tetraalkylammonium hydroxide to provide 3-(3,4-dihydroxyphenyl)-(2S)-[(tert-butoxy)carbonylamino]propanoate tetraalkylammonium salt.

20. The method of claim 19, wherein reacting (2S)-2-amino-3-(3,4-dihydroxyphenyl)propanoic acid with di-tert-butyl dicarbonate and tetraalkylammonium hydroxide to provide 3-(3,4-dihydroxyphenyl)-(2S)-[(tert-butoxy)carbonylamino]propanoate tetraalkylammonium salt is carried out in a mixture of an alcohol and water.

21. The method of claim 20, wherein the mixture of an alcohol and water comprises from about 0%-b.v. to about 4%-b.v. water.

22. The method of claim 20, wherein the alcohol is chosen from methanol, ethanol, isopropanol, and a mixture of any of the foregoing.

23. The method of claim 19, wherein reacting (2S)-2-amino-3-(3,4-dihydroxyphenyl)propanoic acid with di-tert-butyl dicarbonate to provide 3-(3,4-dihydroxyphenyl)-(2S)-[(tert-butoxy)carbonylamino]propanoate tetraalkylammonium salt is carried out at a temperature ranging from about 30° C. to about 50° C.

24. The method of claim 1, wherein reacting 3-(3,4-dihydroxyphenyl)-(2S)-[(tert-butoxy)carbonylamino]propanoate tetraalkylammonium salt with (1R)-2-chloro-isopropyl benzoate in N-methyl-2-pyrrolidone to provide (2R)-2-phenylcarbonyloxypropyl(2S)-3-(3,4-dihydroxyphenyl)-2-[(tert-butoxy)carbonylamino]propanoate is carried out at a temperature of at least 100° C., and provides a yield of (2R)-2-phenylcarbonyloxypropyl(2S)-3-(3,4-dihydroxyphenyl)-2-[(tert-butoxy)carbonylamino]propanoate of at least 40%.

* * * * *